(12) United States Patent
Elbaz et al.

(10) Patent No.: US 9,861,509 B2
(45) Date of Patent: Jan. 9, 2018

(54) DEVICE AND METHODS FOR TREATING A LOWER LIMB JOINT PATHOLOGY AND LOWER LIMB PAIN

(75) Inventors: Avi Elbaz, Dimona (IL); Amit Mor, Rehovot (IL)

(73) Assignee: APOS—Medical and Sports Technologies Ltd., Herzliya (IL)

( * ) Notice: Subject to any disclaimer, the term of this patent is extended or adjusted under 35 U.S.C. 154(b) by 224 days.

(21) Appl. No.: 13/807,149

(22) PCT Filed: Jun. 19, 2011

(86) PCT No.: PCT/IL2011/000487
§ 371 (c)(1),
(2), (4) Date: Mar. 11, 2013

(87) PCT Pub. No.: WO2012/001678
PCT Pub. Date: Jan. 5, 2012

(65) Prior Publication Data
US 2013/0165834 A1    Jun. 27, 2013

Related U.S. Application Data

(60) Provisional application No. 61/359,643, filed on Jun. 29, 2010.

(51) Int. Cl.
*A61F 5/01*    (2006.01)
*A43B 7/00*    (2006.01)
(Continued)

(52) U.S. Cl.
CPC .............. *A61F 5/0127* (2013.01); *A43B 7/00* (2013.01); *A43B 7/144* (2013.01); *A43B 7/146* (2013.01);
(Continued)

(58) Field of Classification Search
CPC ........ A61F 5/01; A61F 5/0102; A61F 5/0104; A61F 5/0106; A61F 5/0111;
(Continued)

(56) References Cited

U.S. PATENT DOCUMENTS

| 1,021,142 A | 3/1912 | Freeman |
| 1,061,353 A | 5/1913 | Block |

(Continued)

FOREIGN PATENT DOCUMENTS

| DE | 1907894 | 1/1965 |
| DE | 29701013 | 3/1997 |

(Continued)

OTHER PUBLICATIONS

ISR from corresponding International Application No. PCT/IL2011/000487; dated Nov. 18, 2011, 13 pages.
(Continued)

*Primary Examiner* — Tarla Patel
(74) *Attorney, Agent, or Firm* — Roach Brown McCarthy & Gruber, P.C.; Kevin D. McCarthy

(57) ABSTRACT

A method of treating a patient suffering from pain in the lower limb or a lower limb musculoskeletal disease is provided. The method includes placement of at least two calibrated, differential disturbances or protuberances under the patient's feet.

27 Claims, 13 Drawing Sheets

(51) Int. Cl.
*A61F 5/32* (2006.01)
*A43B 7/14* (2006.01)
*A43B 13/14* (2006.01)

(52) U.S. Cl.
CPC .......... *A43B 7/1445* (2013.01); *A43B 13/145* (2013.01); *A61F 5/0111* (2013.01); *A61F 5/32* (2013.01); *A61F 2005/0169* (2013.01); *A61F 2005/0179* (2013.01)

(58) Field of Classification Search
CPC ........ A61F 5/0113; A61F 5/0127; A43B 7/00; A43B 7/144; A43B 7/1445; A43B 7/146; A43B 13/146
USPC ............ 602/5, 6, 16, 23, 28, 29; 601/84, 97, 601/101, 102, 104, 112, 113, 118, 119; 36/83, 88, 92, 93, 103, 113, 116, 117.3, 36/117.5, 117.7, 25 R, 27, 28, 29, 31, 36/140, 142, 143, 144, 160
See application file for complete search history.

(56) References Cited

U.S. PATENT DOCUMENTS

| | | | |
|---|---|---|---|
| 1,736,576 A | 11/1929 | Cable | |
| 2,133,302 A | 10/1938 | Mccormick | |
| 2,303,744 A | 12/1942 | Jacobs | |
| 2,311,925 A | 2/1943 | Boos | |
| 2,518,033 A | 8/1950 | Lucas | |
| 3,402,485 A | 9/1968 | Mcmorrow | |
| 3,782,011 A | 1/1974 | Fisher | |
| 3,916,538 A | 11/1975 | Loseff | |
| RE31,173 E | 3/1983 | Daswick | |
| 4,841,648 A | 6/1989 | Shaffer et al. | |
| 4,892,090 A | 1/1990 | Kaeser | |
| 5,188,578 A | 2/1993 | Voigt | |
| 5,337,494 A | 8/1994 | Ricker | |
| 5,400,528 A | 3/1995 | Skinner et al. | |
| 5,533,282 A | 7/1996 | Kataoka et al. | |
| 5,584,787 A | 12/1996 | Guidry | |
| 5,647,145 A | 7/1997 | Russell et al. | |
| 5,682,690 A | 11/1997 | Chang | |
| 5,848,954 A | 12/1998 | Stearns et al. | |
| 6,019,712 A | 2/2000 | Duncan | |
| 6,063,046 A | 5/2000 | Allum | |
| 6,102,832 A | 8/2000 | Tani | |
| 6,170,173 B1* | 1/2001 | Caston .............................. | 36/29 |
| 6,277,057 B1 | 8/2001 | Hayden | |
| 6,283,897 B1 | 9/2001 | Patton | |
| D448,920 S | 10/2001 | Montross et al. | |
| 6,311,416 B1 | 11/2001 | Cohen | |
| 6,349,487 B1 | 2/2002 | Hice | |
| 6,393,735 B1 | 5/2002 | Berggren | |
| 6,511,404 B2 | 1/2003 | Tu | |
| 6,519,873 B1 | 2/2003 | Buttigieg et al. | |
| 6,551,225 B1 | 4/2003 | Romero | |
| 6,652,432 B2 | 11/2003 | Smith | |
| 6,692,419 B2 | 2/2004 | Chen | |
| 6,742,289 B2 | 6/2004 | Celmo | |
| 6,792,703 B2 | 9/2004 | Cohen | |
| 6,811,523 B1 | 11/2004 | Timmer | |
| 6,880,267 B2 | 4/2005 | Smaldone et al. | |
| 6,979,287 B2 | 12/2005 | Elbaz et al. | |
| 7,004,895 B2 | 2/2006 | Perry et al. | |
| 7,101,330 B2 | 9/2006 | Elbaz et al. | |
| 7,165,343 B2 | 1/2007 | Fukui | |
| 7,373,740 B2 | 5/2008 | Lo | |
| 7,500,324 B1 | 3/2009 | Power et al. | |
| 7,707,751 B2 | 5/2010 | Avent et al. | |
| 2002/0026730 A1 | 3/2002 | Whatley | |
| 2002/0038522 A1* | 4/2002 | Houser et al. ..................... | 36/28 |
| 2002/0092201 A1 | 7/2002 | Kraeuter et al. | |
| 2002/0100190 A1 | 8/2002 | Pellerin | |
| 2002/0139011 A1 | 10/2002 | Kerrigan | |
| 2002/0166258 A1 | 11/2002 | Posa | |
| 2003/0148865 A1 | 8/2003 | Handshoe | |
| 2004/0033864 A1 | 2/2004 | Elbaz et al. | |
| 2004/0033874 A1* | 2/2004 | Elbaz ....................... | A43B 5/18 482/148 |
| 2005/0235526 A1 | 10/2005 | Kim | |
| 2007/0051020 A1 | 3/2007 | Tajima et al. | |
| 2007/0079532 A1 | 4/2007 | Ramirez | |
| 2007/0193071 A1 | 8/2007 | Gilmore | |
| 2008/0134541 A1* | 6/2008 | Bar-Haim et al. ................ | 36/27 |
| 2008/0229611 A1 | 9/2008 | Chiodo et al. | |
| 2009/0199429 A1 | 8/2009 | Ellis | |
| 2010/0325919 A1 | 12/2010 | Elbaz et al. | |
| 2011/0126422 A1 | 6/2011 | Vattes et al. | |
| 2012/0073166 A1 | 3/2012 | Bryla | |

FOREIGN PATENT DOCUMENTS

| | | |
|---|---|---|
| DE | 29902731 | 3/2000 |
| DE | 10133863 | 2/2003 |
| EP | 925809 | 6/1999 |
| EP | 2462827 | 6/2012 |
| FR | 1128009 | 1/1957 |
| JP | 2007029700 | 2/2007 |
| KR | 20030058556 | 7/2003 |
| WO | 9620651 | 7/1996 |
| WO | 9713422 | 4/1997 |
| WO | 0067846 | 11/2000 |
| WO | 0137693 | 5/2001 |
| WO | 0237995 | 5/2002 |
| WO | 03090868 | 11/2003 |
| WO | 2004016321 | 2/2004 |
| WO | 2004043185 | 5/2004 |
| WO | 2006005139 | 1/2006 |
| WO | 2011024162 | 3/2011 |
| WO | 2012001685 | 1/2012 |

OTHER PUBLICATIONS

International Search Report and written opinion from the US patent office in a counterpart PCT application—13 pages, dated Nov. 18, 2011.

Examination report from a foreign patent office in a counterpart foreign application—Australian patent application No. 2011272902—dated May 24, 2016—3 pages.

* cited by examiner

DEVICE AND METHODS FOR TREATING A LOWER LIMB JOINT PATHOLOGY AND LOWER LIMB PAIN

FIELD OF INVENTION

This invention is directed to, inter alia, methods of treating a subject afflicted with a lower limb joint pathology.

BACKGROUND OF THE INVENTION

Knee osteoarthritis is the most prevalent type of osteoarthritis in the industrialized world. Over than 30 million Americans suffer from osteoarthritis. In particular, knee osteoarthritis is the most common cause of disability in the United States. Early diagnosis and treatment of knee osteoarthritis are of major importance and can help patients to manage knee osteoarthritis symptoms such as pain and disability and reduce health and health related costs.

The main problem associated with knee osteoarthritis is deterioration of the articular cartilage. Osteoarthritis can be caused by previous injury, repetitive strain on the joint, fractures, ligament tear, and meniscal injury which can affect alignment and promote wear and tear, hereditary factors which cause certain people to develop osteoarthritis, obesity, and subchondral bone deficiencies (the bone layer underneath cartilage)

Medical history, physical examination, and x-rays are used to diagnose osteoarthritis. X-rays are very helpful, allowing the physician to see evidence of osteophytes and joint space narrowing and rule out other causes of pain. If more detailed imaging is needed, an MRI may be ordered. Arthroscopic knee surgery is another way to view the condition of the knee.

Knee osteoarthritis typically develops gradually over a period of years. The primary symptoms associated with knee osteoarthritis include: pain, stiffness, limited range of motion in the knee, and localized swelling. Knee osteoarthritis pain is usually worse following activity, especially overuse of the affected knee. Stiffness can worsen after prolonged periods of resting. As knee osteoarthritis progresses, symptoms generally become more severe.

Currently, osteoarthritis cannot be cured. Most treatments available today involve medications that may help manage the symptoms. Acetaminophen can help manage and relieve pain. Some patients obtain better pain relief when using nonsteroidal anti-inflammatory drugs (NSAIDs) or Celebrex, the one remaining COX-2 selective inhibitor. There are also opioid analgesic medications available for patients who need stronger pain relief.

Aside from medications, other treatments include: local intraarticular injections of steroids or viscosupplements, exercise/physical therapy, weight loss if overweight, topical creams, knee brace or support, heat and cold treatments, glucosamine and chondroitin sulfate, and as a last resort- surgery.

SUMMARY OF THE INVENTION

In one embodiment, the present invention provides a method for treating a subject afflicted with a lower limb joint pathology comprising the steps of: (a) securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to a balanced position, the balanced position being a position whereby the device provides a reduced and/or minimum inversion or a reduced and/or minimum eversion to the subject's foot during the stance phases; and (c) fixing the posterior protuberance and the anterior protuberance to the support member in the balanced position; thereby treating a subject afflicted with lower limb joint pathology.

In one embodiment, the present invention provides a method for treating a subject afflicted with knee osteoarthritis comprising the steps of: (a) securing a device to a subject's foot, whereby the device comprises a foot securing mean, a support member operably attached to the securing mean, and a moveable anterior protuberance and a moveable posterior protuberance; (b) calibrating the posterior protuberance and the anterior protuberance to a balanced position, the balanced position being a position whereby the device provides controlled inversion or controlled eversion to the subject's foot during the stance phases; and (c) fixing the posterior protuberance and the anterior protuberance to the support member in the balanced position; thereby treating a subject afflicted with knee osteoarthritis.

In another embodiment, the present invention further provides a method for treating a subject afflicted with lower limb musculoskeletal pain comprising the steps of: (a) securing a device to the subject's foot, whereby the device comprises a foot securing mean, a support member operably attached to the securing mean, and a moveable anterior protuberance and a moveable posterior protuberance; (b) calibrating the posterior protuberance and the anterior protuberance to a balanced position, the balanced position comprises: a position whereby the device provides a reduced and/or minimum inversion or a reduced and/or minimum eversion to the subject's foot during the stance phases and a minimal lower limb musculoskeletal related pain position; and (c) fixing the posterior protuberance and the anterior protuberance to the support member in the balanced position.

In another embodiment, the present invention further provides a method for treating a subject afflicted with knee pain comprising the steps of: (a) securing a device to the subject's foot, whereby the device comprises a foot securing mean, a support member operably attached to the securing mean, and a moveable anterior protuberance and a moveable posterior protuberance; (b) calibrating the posterior protuberance and the anterior protuberance to a balanced position, the balanced position comprises: a position whereby the device provides controlled inversion or controlled eversion to the subject's foot during the stance phases and a minimal knee related pain position; and (c) fixing the posterior protuberance and the anterior protuberance to the support member in the balanced position; thereby treating a subject afflicted with knee osteoarthritis.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

A Degenerative Joint Disease

Figure 1:
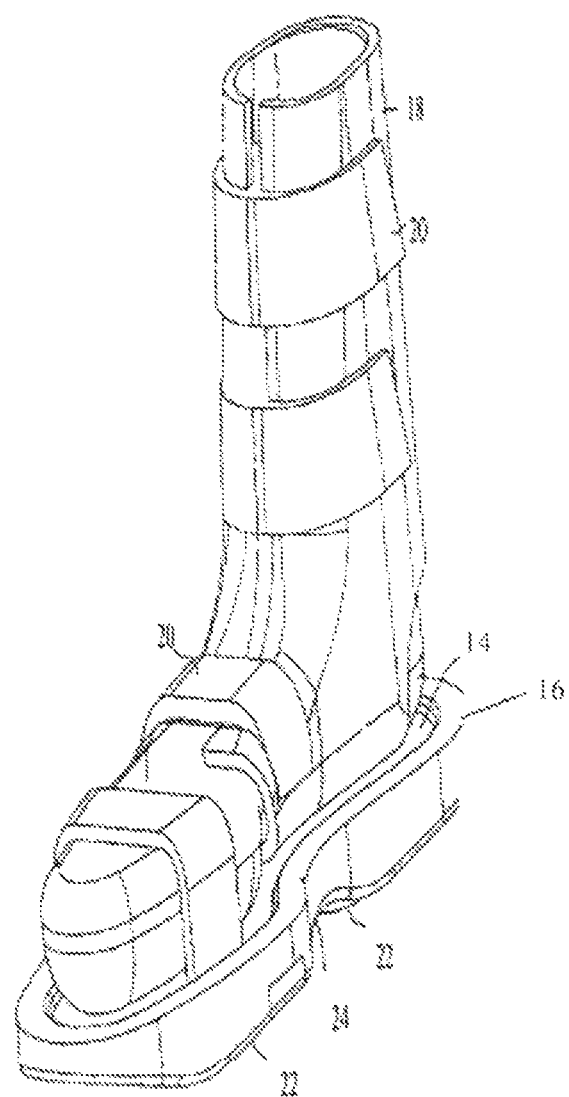
FIG. 1 is a simplified pictorial illustration of footwear constructed and operative in accordance with an embodiment of the present invention

This invention provides, in one embodiment, a method of treating a subject afflicted with a lower limb joint pathology such as but not limited to degenerative joint diseases and musculoskeletal traumas of the lower limb comprising the steps of: (a) Securing a device to a subject's foot, whereby the device comprises a foot securing mean, a support member operably attached to the securing mean, and a moveable anterior bulbous protuberance and a moveable bulbous posterior protuberance; (b) calibrating the posterior protuberance and the anterior protuberance to a balanced position, wherein the balanced position comprises a position whereby the device provides a reduced inversion or a reduced eversion to the subject's foot during the stance phases; and (c) fixing the posterior protuberance and the anterior protuberance to the support member in the balanced position. In another embodiment, a degenerative joint disease is lower limb degenerative joint disease. Each possibility represents a separate embodiment of the present invention.

In another embodiment, provided herein a method based on the notion that calibration of a protuberance supporting an area under a subject foot comprises a therapeutic effect as described herein. In another embodiment, calibrating a protuberance which comprises calibrating convexity, calibrating height, calibrating weight, calibrating position, calibrating resilience or any combination thereof comprises a therapeutic effect according to the methods described herein. Calibrating both an anterior protuberance and a posterior protuberance, in a subject in need thereof, according to the embodiments of the invention comprises a therapeutic effect according to the methods described herein. In another embodiment, placement and calibration of a protuberance comprises the induction of a differential interference during limb locomotion, gait, standing, running, or walking which provides a favorable therapeutic effect according to the methods described herein. In another embodiment, the term "interference" comprises disturbance, interruption, interposition, perturbation, obstruction, or any combination thereof. In another embodiment, the ability to fine-tune an induced interference under a foot of a subject afflicted with a lower limb musculoskeletal disease, disorder, pain or their combination results in treating a disease or alleviating pain stemming from the lower limb or resulting in the lower limb. In another embodiment, provided herein a method of treating a patient suffering from pain in the lower limb or a lower limb musculoskeletal disease by specific placement of at least two calibrated, differential disturbances or protuberances under the patient's feet. In another embodiment, the terms "patient" and "subject" are used interchangeably. Each possibility represents a separate embodiment of the present invention.

In another embodiment, provided herein that the posterior protuberance is a bulbous protuberance. In another embodiment, provided herein that the anterior protuberance is a bulbous protuberance. In another embodiment, provided herein that both the posterior protuberance and the anterior protuberance are bulbous protuberances. Each possibility represents a separate embodiment of the present invention.

In another embodiment, provided herein a method of treating a subject afflicted with a lower limb joint pathology such as but not limited to a lower limb osteoarthritis comprises the steps of: securing a device to a subject's foot, whereby the device comprises a foot securing mean, a support member operably attached to the securing mean, and a moveable anterior protuberance and a moveable posterior protuberance; calibrating the posterior protuberance and the anterior protuberance to a balanced position, the balanced position comprises a position whereby the device provides a reduced inversion or a reduced eversion to the subject's foot during the stance phases; and fixing the posterior protuberance and the anterior protuberance to the support member in the balanced position. In another embodiment, lower limb osteoarthritis is hip osteoarthritis. In another embodiment, lower limb osteoarthritis is ankle osteoarthritis. In another embodiment, lower limb osteoarthritis is foot osteoarthritis. In another embodiment, lower limb osteoarthritis is knee osteoarthritis. In another embodiment, lower limb osteoarthritis is patello-femoral osteoarthritis. In another embodiment, the device provides controllable inversion or a controllable eversion. Each possibility represents a separate embodiment of the present invention.

In another embodiment, a lower limb joint pathology comprises: a lower limb joint disease, a lower limb joint degenerative disease, a lower limb degenerative disease, a lower limb musculoskeletal pathology, a lower limb musculoskeletal trauma, a lower limb musculoskeletal disease, lower limb osteoarthritis, or any combination thereof. In another embodiment, a lower limb joint pathology is associated with lower limb musculoskeletal pain.

In another embodiment, a subject is a human subject. In another embodiment, a subject is a human subject afflicted with a lower limb joint pathology. In another embodiment, a lower limb joint pathology is a hip, an ankle, a foot, or a knee degenerative joint disease. In another embodiment, a lower limb joint pathology comprises a degenerative joint disease such as osteoarthritis. In another embodiment, osteoarthritis is idiopathic osteoarthritis. In another embodiment, a degenerative joint disease is lower limb osteoarthritis. In another embodiment, a degenerative joint disease is knee osteoarthritis. In another embodiment, a hip, an ankle, a foot, or knee osteoarthritis is primary osteoarthritis. Each possibility represents a separate embodiment of the present invention.

In another embodiment, a degenerative joint disease is foot osteoarthritis. In another embodiment, a degenerative joint disease is hip osteoarthritis. In another embodiment, osteoarthritis is secondary osteoarthritis. In another embodiment, knee osteoarthritis is secondary knee osteoarthritis. In another embodiment, classification into either primary or secondary depends on if there is or is not an identifiable underlying cause. Each possibility represents a separate embodiment of the present invention.

In another embodiment, a lower limb joint pathology is patellar compression. In another embodiment, a lower limb joint pathology is joint line tenderness. In another embodiment, a lower limb joint pathology is joint line effusion. In another embodiment, a lower limb joint pathology is patellar tendonitis. In another embodiment, a lower limb joint pathology is infrapatellar tendonitis. In another embodiment, a lower limb joint pathology is pain and/or tenderness in any patellar or prepatellar anatomical structure. Each possibility represents a separate embodiment of the present invention. In another embodiment, tendonitis is tendon degeneration. In another embodiment, tendonitis is tendinosis. In another embodiment, tendonitis is pain arising from the tendon due degenerative changes in the tendon.

In another embodiment, a lower limb joint pathology is a lower limb degenerative joint disease. In another embodiment, a lower limb joint pathology is medial/lateral/patella-femoral osteoarthritis (OA) or any combination thereof (primary or secondary). In another embodiment, a lower limb joint pathology is Pes-anserinus bursitis. In another embodiment, a lower limb joint pathology is characterized by anterior knee pain and/or patello-femoral pain. In another embodiment, a lower limb joint pathology is a meniscal tear (both degenerative and traumatic). In another embodiment, a lower limb joint pathology is ligament tear/partial tear/strain/post reconstruction (ACL, PCL, MCL, LCL), or any combination thereof. In another embodiment, a lower limb joint pathology includes pre/post arthroplasty including total, hemi, or resurfacing and use of the methods as described herein. In another embodiment, a lower limb joint pathology is tibial plateau fracture. In another embodiment, a lower limb joint pathology is osteonecrosis (both in the tibia and femur). In another embodiment, a lower limb joint pathology is Patelar tendonitis. In another embodiment, a lower limb joint pathology is Osgood schlatter. In another embodiment, a lower limb joint pathology comprises post lower limb surgery. Each possibility represents a separate embodiment of the present invention.

In another embodiment, a lower limb joint pathology is hip replacement. In another embodiment, a lower limb joint pathology is hip resurfacing. In another embodiment, a lower limb joint pathology is pre-patellar bursitis. In another embodiment, a lower limb joint pathology is trochanteric bursitis. In another embodiment, a lower limb joint pathology comprises necrosis within the lower limb joint. In another embodiment, a lower limb joint pathology comprises hip fracture. In another embodiment, a lower limb joint pathology comprises developmental dysplasia of the hip. In another embodiment, a lower limb joint pathology comprises tendonitis/tendinosis of the hip. In another embodiment, a lower limb joint pathology comprises impingement of the hip. Each possibility represents a separate embodiment of the present invention.

In another embodiment, a lower limb joint pathology comprises Osteochondritis dissecans of the foot or ankle. In another embodiment, a lower limb joint pathology comprises acute or chronic instability of the foot or ankle. In another embodiment, a lower limb joint pathology comprises Ligament Sprain, tear, and/or repair within a joint of the foot or ankle. In another embodiment, a lower limb joint pathology comprises a foot or ankle fracture. In another embodiment, a lower limb joint pathology comprises Plantar Fascitis. In another embodiment, a lower limb joint pathology comprises Tibialis posterior insufficiency and/or dysfunction. In another embodiment, a lower limb joint pathology comprises a pronating foot. In another embodiment, a lower limb joint pathology comprises a supinating foot. In another embodiment, a lower limb joint pathology comprises of pes planus or pes cavus. Each possibility represents a separate embodiment of the present invention.

In another embodiment, a lower limb joint pathology comprises ilio-tibial band (ITB) syndrome. In another embodiment, a lower limb joint pathology comprises hyperlaxity or hypermobility. In another embodiment, a lower limb joint pathology comprises muscular atrophy. In another embodiment, a lower limb joint pathology comprises tumors within a lower limb. In another embodiment, a lower limb joint pathology comprises tumors which affect a joint of the lower limb. Each possibility represents a separate embodiment of the present invention.

In another embodiment, treating or treatment according to the invention comprises diminishing, alleviating, reducing, inhibiting, improving, reversing, and/or ameliorating: pain, stiffness, swelling, inflammation, cartilage degeneration, osteophytes, narrowing of joint space, effusion, muscular atrophy, deterioration of neuro-muscular control, deterioration of proprioception bracing, pathological moments, gait disorders, limping, compensatory gait, antalgic gait, asymmetry in gait, guarding of muscles, loosening of ligaments, loosening of joint capsule, stretching of ligaments, stretching of joint capsule, reduced step length, reduced single limb support, increased single limb support, reduced gait velocity, or any combination thereof. In another embodiment, treating or treatment according to the invention comprises diminishing, alleviating, reducing, inhibiting, improving, reversing, and/or ameliorating bone marrow edema, lesions, subchondral bone changes, softening of cartilage, fibrillating and thinning of cartilage, ebornation of the bone, or any combination thereof. Each possibility represents a separate embodiment of the present invention.

In another embodiment, treating or treatment comprise performing a variety of maneuvers in a proprioceptive and/or kinesthetic exercise plan for the foot, leg, upper leg, lower back and even upper torso and other body parts and organs. In another embodiment, treating or treatment comprise performing a variety of walking and or gait exercise plan for the foot, upper leg, lower back and even upper torso and other body parts and organs. Each possibility represents a separate embodiment of the present invention.

In another embodiment, the subject is suffering from pain stemming from a lower limb joint pathology. In another embodiment, the subject is suffering from pain, a joint pain, tenderness, stiffness, locking, an effusion, or any combination thereof. In another embodiment, the subject is suffering from loss of cartilage. In another embodiment, the subject is suffering from a decreased movement secondary to pain. In another embodiment, the subject is suffering from regional muscles atrophy. In another embodiment, the subject is suffering from lax ligaments. In another embodiment, the subject is suffering from crackling noise ("crepitus") when the affected joint is moved or touched. In another embodiment, the subject is suffering from muscle spasm or bracing. In another embodiment, the subject is suffering from tendons contractions. In another embodiment, the methods as described alleviate a painful joint. In another embodiment, the methods as described treat the underlying causes of joint pain. Each possibility represents a separate embodiment of the present invention.

Osteoarthritis

In another embodiment, the subject is suffering from osteoarthritis. In another embodiment, the subject is suffering from lower limbs osteoarthritis. In another embodiment, the subject is suffering from hips osteoarthritis. In another embodiment, the subject is suffering from spine osteoarthritis. In another embodiment, the subject is suffering from feet osteoarthritis. In another embodiment, the subject is suffering from a joint effusion (water in the knee in lay terms). Each possibility represents a separate embodiment of the present invention.

In another embodiment, the subject is at risk of being afflicted with osteoarthritis. In another embodiment, the subject is exposed to elevated mechanical stress on the joints. In another embodiment, the subject is afflicted with misalignments of bones caused by congenital or pathogenic causes. In another embodiment, the subject is overweight or obese. In another embodiment, the subject suffers from loss of strength in muscles supporting joints, impairment of peripheral nerves, uncoordinated movements that overstress joints, ligaments, muscles, tendons, or any combination thereof. Each possibility represents a separate embodiment of the present invention.

In another embodiment, the subject is afflicted with osteophytes. In another embodiment, the methods as described herein inhibit narrowing of the joint space. In another embodiment, the methods as described herein expand the joint space. In another embodiment, the methods as described herein inhibit increased subchondral bone density. In another embodiment, the methods as described herein decrease subchondral bone density. In another embodiment, the methods as described herein increase the water content of the cartilage. In another embodiment, the methods as described herein increase proteoglycan content of the cartilage. In another embodiment, the methods as described herein inhibit inflammation of the surrounding joint capsule. In another embodiment, the methods as described herein inhibit "spurs" or osteophytes that form on the margins of the joints. In another embodiment, the methods as described herein are used as a prevention measure for subjects at risk of being afflicted with osteoarthritis. In another embodiment, subjects at risk of being afflicted with osteoarthritis are subjects of whose siblings are afflicted with osteoarthritis. Each possibility represents a separate embodiment of the present invention.

In another embodiment, osteoarthritis is primary generalized nodal osteoarthritis. In another embodiment, osteoarthritis is erosive osteoarthritis. In another embodiment, osteoarthritis is inflammatory osteoarthritis. In another embodiment, osteoarthritis is secondary osteoarthritis that is caused by other factors but the resulting pathology is the same as for primary osteoarthritis. Each possibility represents a separate embodiment of the present invention.

In another embodiment, lower limb osteoarthritis (OA) is characterized by pain, stiffness, swelling, inflammation, cartilage degeneration, osteophytes, narrowing of joint space, effusion, muscular atrophy, deterioration of neuromuscular control, deterioration of proprioception, bracing, pathological moments, gait disorders, limping, compensatory gait, antalgic gait, asymmetry in gait, guarding of muscles, loosening of ligaments, loosening of joint capsule, stretching of ligaments, stretching of joint capsule, reduced step length, or any combination thereof. Each possibility represents a separate embodiment of the present invention.

Lower Limb Musculoskeletal Pain

In another embodiment, "pain" as used herein comprises a sharp ache. In another embodiment, "pain" as used herein comprises a burning sensation in the associate muscles and tendons. In another embodiment, "pain" as used herein comprises continuous pain. In another embodiment, "pain" as used herein comprises is a momentary pain. In another embodiment, "pain" as used herein comprises seasonal pain (winter, summer or change of weather). In another embodiment, "pain" as used herein comprises activity specific pain such as sports or any other physical activity related pain. Each possibility represents a separate embodiment of the present invention.

In another embodiment, provided herein a method of treating a subject afflicted with a lower limb musculoskeletal pain comprising the steps of: steps of: securing a device to the subject's foot, whereby the device comprises a foot securing mean, a support member operably attached to the securing mean, and a moveable anterior protuberance and a moveable posterior protuberance; calibrating the posterior protuberance and the anterior protuberance to: (1) a balanced position, the balanced position comprises: a position whereby the device provides a minimal inversion or a minimal eversion to the subject's foot during the stance phases; and (2) a minimal lower limb musculoskeletal related pain position; and fixing the posterior protuberance and the anterior protuberance to the support member in the balanced position. Each possibility represents a separate embodiment of the present invention. In another embodiment, the term "minimal" comprises reduced or least.

In another embodiment, provided herein a method of treating a subject afflicted with a lower limb musculoskeletal pain comprising the steps of: securing a device to the subject's foot, whereby the device comprises a foot securing mean, a support member operably attached to the securing mean, and a moveable anterior protuberance and a moveable posterior protuberance; calibrating the posterior protuberance and the anterior protuberance to: (1) a balanced position, the balanced position comprises: a position whereby the device provides a controlled inversion or a controlled eversion to the subject's foot during the stance phases; and (2) a minimal lower limb musculoskeletal related pain position; and fixing the posterior protuberance and the anterior protuberance to the support member in the balanced position. Each possibility represents a separate embodiment of the present invention.

In another embodiment, lower limb musculoskeletal pain comprises anterior knee pain. In another embodiment, lower limb musculoskeletal pain comprises patello-femoral knee pain. Each possibility represents a separate embodiment of the present invention.

In another embodiment, a lower limb musculoskeletal pain arises from two types of trauma, acute trauma and cumulative (overuse) trauma. In another embodiment, acute traumas occur when the load imposed on the body during a task exceeds the tolerance of the body structures supporting it. In another embodiment, a lower limb musculoskeletal pain is associated with large single loading conditions. In another embodiment, a lower limb musculoskeletal pain is a violent lateral impact on a joint such as but not limited to the knee. In another embodiment, a lower limb musculoskeletal pain is an infrequent extreme force exertion on a joint. In another embodiment, overuse trauma, occurs when the load imposed on the body during a task is not large enough to cause sudden failure of one or other of the underlying body structures (bone, the muscles, tendons and ligaments) but instead these structures are worn down and their tolerance lowered with repeated application of the load. In another embodiment, a lower limb musculoskeletal pain is caused by "wear and tear" on the bodily structures. Each possibility represents a separate embodiment of the present invention.

In another embodiment, a lower limb musculoskeletal pain arises from stress fractures and shin splints. In another embodiment, a lower limb musculoskeletal pain arises from ankle and metacarpal fractures (acute injuries). In another embodiment, a lower limb musculoskeletal pain arises from bursitis. In another embodiment, a lower limb musculoskeletal pain arises from rheumatism. In another embodiment, a lower limb musculoskeletal pain arises from cartilage tear. Each possibility represents a separate embodiment of the present invention.

In another embodiment, a lower limb musculoskeletal pain is a consequence of lower limb osteoarthritis. In another embodiment, a lower limb musculoskeletal pain is a consequence of Piriformis syndrome. In another embodiment, a lower limb musculoskeletal pain is a consequence of Trochanteritis. In another embodiment, a lower limb musculoskeletal pain is sacroiliac pain. In another embodiment, a lower limb musculoskeletal pain causes palpable tenderness of the trochanter major. In another embodiment, a lower limb musculoskeletal pain is caused by hamstring muscle strain. In another embodiment, a lower limb musculoskeletal pain is caused by hamstring injuries. Each possibility represents a separate embodiment of the present invention.

In another embodiment, a lower limb musculoskeletal pain is a direct consequence of bursitis. In another embodiment, a lower limb musculoskeletal pain is a direct consequence of a beat knee (Hyperkeratosis). In another embodiment, a lower limb musculoskeletal pain is a direct consequence of a meniscal lesion. In another embodiment, a lower limb musculoskeletal pain is a direct consequence of meniscal damage. In another embodiment, a lower limb musculoskeletal pain is a direct consequence of a degenerative joint disease. In another embodiment, a lower limb musculoskeletal pain is a direct consequence of a lower limb degenerative joint disease. Each possibility represents a separate embodiment of the present invention.

In another embodiment, a lower limb musculoskeletal pain is a direct consequence of bursitis (Adventitious, prepatellar, etc). In another embodiment, bursitis develops in response to frictional stress that is applied directly over the bursa of the knees. In another embodiment, bursitis is pyogenic bursitis. In another embodiment, a lower limb musculoskeletal pain is associated with tenderness and swelling over the patella. Each possibility represents a separate embodiment of the present invention.

In another embodiment, a lower limb musculoskeletal pain is a direct consequence of hyperkeratosis. In another embodiment, hyperkeratosis is an acute and extreme form of bursitis. Each possibility represents a separate embodiment of the present invention.

In another embodiment, a lower limb musculoskeletal pain is a direct consequence of meniscal lesions and/or damage. In another embodiment, meniscal lesions/damage usually occurs due to high rates of force being applied to the knee, or heavy rotational force, e.g. when the knee is bent or twisted while bearing load. Each possibility represents a separate embodiment of the present invention.

In another embodiment, a lower limb musculoskeletal pain is a direct consequence of stress fracture/stress reaction injuries. In another embodiment, the term 'stress reaction' refers to bone with evidence of remodeling but with an absence of radiological evidence of fracture. In another embodiment, stress reaction/fracture is the result of repeated micro-injuries to bone, which occur when its maximum strength is exceeded by an applied force and the natural process by which bone adapts to stress is prevented. In another embodiment, stress fracture is associated with the tibia or femur or foot. In another embodiment, stress fracture is associated with the fibula. Each possibility represents a separate embodiment of the present invention.

In another embodiment, a lower limb musculoskeletal pain is a direct consequence of a sprained ankle. In another embodiment, a lower limb musculoskeletal pain is a direct consequence of an anterior compartment syndrome. In another embodiment, a lower limb musculoskeletal pain is a direct consequence of a lateral compartment syndrome. In another embodiment, a lower limb musculoskeletal pain is a direct consequence of a plantar Fasciitis. In another embodiment, a lower limb musculoskeletal pain is a direct consequence of an Achilles Tendonitis. In another embodiment, a lower limb musculoskeletal pain is a direct consequence of a foot corns. In another embodiment, a lower limb musculoskeletal pain is a direct consequence of Halux Valgus. In another embodiment, a lower limb musculoskeletal pain is a direct consequence of interdigital neuroma. In another embodiment, a lower limb musculoskeletal pain is a direct consequence of tarsal tunnel syndrome. In another embodiment, a lower limb musculoskeletal pain is a direct consequence of a lesser toe deformity. In another embodiment, a lower limb musculoskeletal pain is a direct consequence of psoriatic arthritis. Each possibility represents a separate embodiment of the present invention.

In another embodiment, a lower limb musculoskeletal pain is heel pain. In another embodiment, a lower limb musculoskeletal pain is a direct consequence of an acquired flatfoot. In another embodiment, a lower limb musculoskeletal pain is associated with a putative genesis in abnormal foot pronation. In another embodiment, a lower limb musculoskeletal pain is associated with defective gait patterns. In another embodiment, a lower limb musculoskeletal pain is associated with defective stance. Each possibility represents a separate embodiment of the present invention.

The Subject

In another embodiment, the subject is afflicted with a congenital disorder of joints. In another embodiment, the subject is afflicted with diabetes. In another embodiment, the subject is afflicted with inflammatory diseases (such as Perthes' disease, Lyme disease, a chronic form of arthritis). Each possibility represents a separate embodiment of the present invention.

In another embodiment, the subject is afflicted with rheumatoid arthritis. In another embodiment, the subject is afflicted with Achilles tendon injuries and Tendonitis In another embodiment, the subject is afflicted with adductor strain. In another embodiment, the subject is afflicted with an ankle sprain. In another embodiment, the subject is afflicted with anterior cruciate ligament injury. In another embodiment, the subject is afflicted with calcaneal bursitis. In another embodiment, a lower limb musculoskeletal pain is coccyx pain. In another embodiment, the subject is afflicted with compartment syndrome. In another embodiment, the subject is afflicted with iliotibial band syndrome. In another embodiment, the subject is afflicted with medial collateral and lateral collateral ligament injury. In another embodiment, the subject is afflicted with Meralgia Paresthetica. In another embodiment, the subject is afflicted with Morton Neuroma. In another embodiment, the subject is afflicted with Osteitis Pubis. In another embodiment, the subject is afflicted with patellofemoral syndrome. In another embodiment, the subject is afflicted with Pes Anserinus bursitis or tendonitis. In another embodiment, the subject is afflicted with Piriformis syndrome. In another embodiment, the subject is afflicted with plantar Fasciitis. In another embodiment, the subject is afflicted with posterior cruciate ligament injury. In another embodiment, the subject is afflicted with prepatellar bursitis. In another embodiment, the subject is afflicted with Trochanteric bursitis. Each possibility represents a separate embodiment of the present invention.

In another embodiment, a subject according to the invention further suffers from a gait disorder. In another embodiment, a subject according to the invention is a human subject that can walk or run with a device as described herein. In another embodiment, a subject according to the invention is a human subject that can walk or run with footwear 10. Each possibility represents a separate embodiment of the present invention. In another embodiment, a gait disorder is asymmetry of gait, shuffling gait, gait with lurching actions, or any combination thereof. In another embodiment, a gait disorder is caused by a degenerative joint disease. Each possibility represents a separate embodiment of the present invention.

Treatment

In another embodiment, the method as described herein involves exercise with the device as described herein. In another embodiment, exercise is walking or any other form of gait movement. In another embodiment, improvement in measured in a gait lab. In another embodiment, improvement in subject's physical state is observed by using the methods described herein. In another embodiment, treating is improvement in subject's physiological state. In another embodiment, treating is improvement in subject's mental state. In another embodiment, treating is improvement in subject's wellbeing. In another embodiment, treating is relieving pain such as joint pain. In another embodiment, treating is relieving tenderness. In another embodiment, treating is relieving stiffness. In another embodiment, treating is relieving locking. In another embodiment, treating is relieving an effusion. In another embodiment, treating is inhibiting loss of cartilage. In another embodiment, treating is inducing de-novo cartilage build-up. In another embodiment, treating is increasing movement. In another embodiment, treating is increasing movement secondary to pain. In another embodiment, treating is inhibiting regional muscles atrophy. In another embodiment, treating is reversing regional muscles atrophy. In another embodiment, treating is inducing muscle build-up. In another embodiment, treating is inducing differential muscle build-up. Each possibility represents a separate embodiment of the present invention.

In another embodiment, treating is improving gait. In another embodiment, treating is improving balance. In another embodiment, treating is improving impairments of proprioception, balance, strength, or any combination thereof. In another embodiment, treating is reversing impairments of proprioception, balance, strength, or any combination thereof. In another embodiment, treating is specifically improving impairments of proprioception, balance, strength, or any combination thereof associated with a specific degenerative joint disease. In another embodiment, treating is specifically improving impairments of proprioception, balance, strength, or any combination thereof associated with lower extremity arthritis. In another embodiment, treating is specifically improving impairments of proprioception, balance, strength, or any combination thereof associated with a hip, an ankle, a foot, or knee osteoarthritis. In another embodiment, treating is reducing falls. Each possibility represents a separate embodiment of the present invention.

In another embodiment, treating is manipulating a step length. In another embodiment, treating is decreasing "step length difference". In another embodiment, treating is manipulating single limb support. In another embodiment, treating is manipulating out/in towing angle. In another embodiment, treating is calibrating gait cycle (40:40:20). In another embodiment, treating is manipulating cadence. In another embodiment, treating is manipulating the center of pressure (COP). In another embodiment, treating is correcting mean hip motion, knee motion, ankle motion, or any combination thereof in the sagittal, frontal, and transverse planes. In another embodiment, treating is improving walking pace or speed. In another embodiment, treating is enhancing walking pace or speed. In another embodiment, improving walking pace or speed is reaching a goal of walking speed of 1.6-4 km/hour. In another embodiment, improving walking pace or speed is reaching a goal of walking speed of 1.6-4 km/hour for at least 2 minutes. In another embodiment, improving walking pace or speed is reaching a goal of walking speed of 1.6-4 km/hour for at least 5 minutes. In another embodiment, improving walking pace or speed is reaching a goal of walking speed of 1.6-4 km/hour for at least 10 minutes. In another embodiment, improving walking pace or speed is reaching a goal of walking speed of 1.6-4 km/hour for at least 15 minutes. In another embodiment, improving walking pace or speed is reaching a goal of walking speed of 2-3.5 km/hour for at least 2 minutes. In another embodiment, improving walking pace or speed is reaching a goal of walking speed of 2-3.5 km/hour for at least 5 minutes. In another embodiment, improving walking pace or speed is reaching a goal of walking speed of 2-3.5 km/hour for at least 10 minutes. In another embodiment, improving walking pace or speed is reaching a goal of walking speed of 2-3.5 km/hour for at least 15 minutes. In another embodiment, improving walking pace or speed is reaching a goal of walking speed of 2.5-3.2 km/hour for at least 2 minutes. In another embodiment, improving walking pace or speed is reaching a goal of walking speed of 2.5-3.2 km/hour for at least 5 minutes. In another embodiment, improving walking pace or speed is reaching a goal of walking speed of 2.5-3.2 km/hour for at least 10 minutes. In another embodiment, improving walking pace or speed is reaching a goal of walking speed of 2.5-3.2 km/hour for at least 15 minutes. Each possibility represents a separate embodiment of the present invention.

In another embodiment, treating is relaxing a stiff knee, hip, ankle, or foot. In another embodiment, treating is correcting an abnormal flexion or extension in stance phase. In another embodiment, treating is correcting a restriction of hip extension in toe-off. In another embodiment, treating is correcting an abnormal muscle activity of the lower limb. In another embodiment, treating is correcting overactivity of quadriceps in stance. In another embodiment, treating is correcting (shortening or lengthening) semitendinosus activity. In another embodiment, treating is correcting exaggerated triceps surae activity in swing. In another embodiment, treating is correcting a silent tibialis anterior in terminal swing. In another embodiment, treating is toning any lower limb muscle. Each possibility represents a separate embodiment of the present invention.

In another embodiment, the methods as described herein further comprises a combination treatment comprising the use of the device as described herein and a proper medication. In another embodiment, one of skill in the art will readily diagnose and prescribe the proper medication to a subject suffering from a disease or a condition such as described herein. In another embodiment, the medication is an analgesic such as acetaminophen. In another embodiment, the medication is a non-steroidal anti-inflammatory drug (NSAID) such as ibuprofen. In another embodiment, the medication is a COX-2 selective inhibitor such as celecoxib. In another embodiment, the medication is a topical NSAID such as diclofenac. In another embodiment, the medication is an opioid analgesic such as morphine or codeine. In another embodiment, the medication is a glucocorticoid such as hydrocortisone injected into the knee. In another embodiment, the medication is topical capsaicin. In another embodiment, the medication is a joint injection of hyaluronic acid. Each possibility represents a separate embodiment of the present invention.

In another embodiment, the outcome of treatment as provided herein is apparent immediately after the initial use of the device as described herein. In another embodiment, the outcome of treatment as provided herein is apparent after 10-1000000 meters of walking with the device as described herein. In another embodiment, the outcome of treatment as provided herein is apparent after 50-100000 meters of walking with the device as described herein. In another embodiment, the outcome of treatment as provided herein is apparent after 500-10000 meters of walking with the device as described herein. In another embodiment, the outcome of treatment as provided herein is apparent after 500-5000 meters of walking with the device as described herein. In another embodiment, the outcome of treatment as provided herein is apparent after 500-3000 meters of walking with the device as described herein. Each possibility represents a separate embodiment of the present invention.

In another embodiment, the outcome of treatment as provided herein is correction of a pathology related to lower limb osteoarthritis. In another embodiment, the outcome of treatment as provided herein is correction of a hip, an ankle, a foot, or a knee osteoarthritis. In another embodiment, the outcome of treatment as provided herein is elevating lower limb osteoarthritis. In another embodiment, the outcome of treatment as provided herein is inhibiting symptoms associated with lower limb osteoarthritis. Each possibility represents a separate embodiment of the present invention.

In another embodiment, the outcome of treatment as provided herein is apparent while the subject is wearing the device as described herein. In another embodiment, the outcome of treatment as provided herein is apparent also when the subject is walking barefoot. In another embodiment, the outcome of treatment as provided herein is apparent also when the subject is wearing walking shoes. In another embodiment, the outcome of treatment as provided herein is apparent also when the subject is wearing work shoes (including but not limited to elegant shoes). Each possibility represents a separate embodiment of the present invention.

In another embodiment, differential muscle build-up comprises inducing muscle build-up in regions of muscles atrophy. In another embodiment, differential muscle build-up comprises inducing muscle build-up in regions of muscles weakness. In another embodiment, differential muscle build-up comprises inducing muscle build-up in regions of muscles injury. Each possibility represents a separate embodiment of the present invention.

In another embodiment, a device as disclosed herein has an immediate effect with regard to treating or treatment of a disease, a pathology, and/or pain as provided herein. In another embodiment, short term immediate effect is apparent in a barefoot subject after walking with the device for 1-5 minutes. In another embodiment, a device as disclosed herein has an immediate effect with regard to treating or treatment of a disease, a pathology, and/or pain as provided herein. In another embodiment, short term immediate effect is apparent in a barefoot subject after walking with the device for 10-60 minutes. In another embodiment, short term immediate effect is apparent in a barefoot subject after walking with the device for 30-600 minutes. In another embodiment, short term immediate effect is apparent in a barefoot subject after walking with the device for 1-10 hours (hrs). In another embodiment, short term immediate effect is apparent in a barefoot subject after walking with the device for 5-1000 hours (hrs). In another embodiment, short term immediate effect is apparent in a barefoot subject after walking with the device for 12-96 hours (hrs). In another embodiment, short term immediate effect is apparent in a barefoot subject after walking with the device for 1-10 days. In another embodiment, short term immediate effect is apparent in a barefoot subject after walking with the device for 7-21 days. In another embodiment, short term immediate effect is apparent in a barefoot subject after walking with the device for 5-30 days. Each possibility represents a separate embodiment of the present invention.

In another embodiment, the effect is apparent in a barefoot subject after walking with the device for 1-2 months. In another embodiment, the effect is apparent in a barefoot subject after walking with the device for 1-24 months. In another embodiment, the effect is apparent in a barefoot subject after walking with the device for 2-6 months. In another embodiment, the effect is apparent in a barefoot subject after walking with the device for 4-10 months. In another embodiment, the effect is apparent in a barefoot subject after walking with the device for 6-48 months. In another embodiment, the effect is apparent in a barefoot subject after walking with the device for 12-24 months. In another embodiment, the effect is apparent in a barefoot subject after walking with the device for 10-30 months. Each possibility represents a separate embodiment of the present invention.

In another embodiment, treating is a process wherein the subject's disease or condition is ameliorated. In another embodiment, treating is improvement over time. In another embodiment, treating is continuous improvement over time. In another embodiment, progress or improvement is reduction in any measure provided herein. In another embodiment, progress or improvement is measured in a gait lab. In another embodiment, progress or improvement is measured by radiological methods. In another embodiment, radiological methods for measuring progress, treatment and/or improvement are known to one of skill in the art (such as but not limited to: X-ray, MRI, etc.). In another embodiment, progress or improvement is measured by a pain questionnaire. In another embodiment, progress or improvement is measured by physical examination that includes examining a range of motions such as but not limited to: flexion, extension, dorsi/plantar flexion (ankle), muscular circumference, internal/external rotation (hip) abduction/adducton (hip and knee), effusion, hot/warm knee, or any combination thereof. In another embodiment, progress or improvement is measured by visual clinical gait assessment. Each possibility represents a separate embodiment of the present invention.

In another embodiment, progress or improvement is measured in a gait lab and includes measuring velocity, step length increase, step length difference (symmetry), single limb support (aim at reaching 40%), single limb support difference (symmetry), double limb support, in-toeing/out-toeing, flexion/extension, range of motion (rom), flexion/extension, or any combination thereof. Each possibility represents a separate embodiment of the present invention.

In another embodiment, a device as described herein is prescribed to a subject according to the subject's physical condition. In another embodiment, a device as described herein is prescribed to a subject according to the subject's medical condition. In another embodiment, a device as described herein is prescribed to a subject according to the subject's medical history. In another embodiment, prescription includes directions of how to use the device. In another embodiment, prescription includes intensity of use, daily use, or daily distance directions. In another embodiment, prescription to a subject having step length of 45 cm or less comprises usage of the device by walking for 10-40 minutes a day. In another embodiment, prescription to a subject having step length of 45 cm or less comprises usage of the device by walking for 10-40 minutes every other day. Each possibility represents a separate embodiment of the present invention.

In another embodiment, medium prescription applies to subjects having step length of 45-60 cm. In another embodiment, medium prescription applies to subjects having step length of 50-60 cm. In another embodiment, medium prescription applies to subjects having step length of 60-65 cm. In another embodiment, medium prescription comprises usage of the device by walking for 5-20 minutes a day. In another embodiment, medium prescription comprises usage of the device by walking for 10-20 minutes a day. In another embodiment, medium prescription comprises usage of the device by walking for 5-15 minutes a day. Each possibility represents a separate embodiment of the present invention.

In another embodiment, high prescription applies to subjects having step length of 65 cm and above. In another embodiment, high prescription applies to subjects having step length of 60 cm and above. In another embodiment, high prescription comprises usage of the device by walking for 5-20 minutes a day. In another embodiment, high prescription comprises usage of the device by walking for 10-20 minutes a day. In another embodiment, high prescription comprises usage of the device by walking for 5-15 minutes a day. Each possibility represents a separate embodiment of the present invention.

In another embodiment, any prescription as described herein comprises increase in daily usage time as the subject's step length improves. In another embodiment, any prescription as described herein comprises increase in daily usage time as the subject's functional level improves. In another embodiment, any prescription as described herein comprises increase in daily usage time as subject's pain decreases. In another embodiment, any prescription as described herein comprises increase in daily usage time as subject's disease or condition as described herein, improves. In another embodiment, a prescription as described herein further comprises medicating the subject according to his or hers medical condition. Each possibility represents a separate embodiment of the present invention.

In another embodiment, a prescription as described herein further comprises adjustments of the device as subject's disease or condition improved or deteriorates. In another embodiment, adjustments of the device comprise calibrating or positioning a protuberance as described herein. Each possibility represents a separate embodiment of the present invention.

The Device

In another embodiment, the device is secured to a subject's foot directly. In another embodiment, the term "secured to a subject's foot" comprises securing the device to any footwear such as but not limited to shoes, boots, etc that are secured to a subject's foot. In another embodiment, a foot securing means secures the device such as footwear 10 to a subject's foot. In another embodiment, various different feet securing means can be used. In another embodiment, a foot securing mean comprises a plurality of securing means. In another embodiment, a foot securing mean is a lace. In another embodiment, a foot securing mean comprises a Velcro fastener. In another embodiment, a foot securing mean comprises securing straps. In another embodiment, reference is made to FIGS. 1-4, which illustrate footwear 10 constructed and operative in accordance with an embodiment of the present invention. Each possibility represents a separate embodiment of the present invention.

In another embodiment, a support member is operably attached to the securing mean. In another embodiment, operably attached comprises sufficient attachment between the securing mean and the support member. In another embodiment, a support member comprises the sole. In another embodiment, a support member comprises the inner sole. In another embodiment, a support member comprises the outer sole. In another embodiment, a support member comprises the middle sole. In another embodiment, a support member comprises the upper (the part of the shoe that is on top of the foot). In another embodiment, the upper is operably attached to the securing mean (such as but not limited to laces). In another embodiment, the upper comprises straps or totally enclosing the foot.). In another embodiment, the upper comprises straps that function as securing means (such as sandals). Each possibility represents a separate embodiment of the present invention.

In another embodiment, a device such as footwear 10 is supplied as one or more pairs of shoe-like devices, or alternatively, as just one of the shoe-like devices. In another embodiment, footwear 10 comprises a support member 12 having a periphery in a shape of a shoe sole comprising an upper surface 14. In the illustrated embodiment, the upper surface 14 is indented with a peripheral ridge 16, but it is appreciated that other configurations of upper surface 14 are within the scope of the invention. In another embodiment, footwear 10 is attached to a foot of a user by means of a boot 18 and/or fasteners 20, such as but not limited to, VELCRO straps, buckles, shoe laces, and the like. In another embodiment, footwear 10 is attached to a foot of a user by means of a shoe. In another embodiment, a shoe comprises a platform of a sneaker. In another embodiment, the term sneaker comprises a boot. In another embodiment, the term sneaker comprises a walking boot. In another embodiment, a shoe comprises a platform of a running shoe. In another embodiment, a shoe comprises a platform of an elegant shoe. In another embodiment, a shoe comprises a platform of a walking shoe or boot. Each possibility represents a separate embodiment of the present invention.

In another embodiment, a device such as but not limited to boot 18 is fashioned for attachment to the user's foot with or without fasteners 20. In another embodiment, fasteners 20 are used as foot securing means to attach footwear 10 to the user's foot without boot 18. Each possibility represents a separate embodiment of the present invention.
BP
In another embodiment, the invention provides that the device such as footwear comprises protuberances in a fixed position. In another embodiment, the invention provides that the device such as footwear 10 comprises protuberances having any shape known to one of skill in the art. In another embodiment, the invention provides that the device comprises at least two bulbous protuberances. In another embodiment, a protuberance is symmetrical. In another embodiment, a protuberance is asymmetrical In another embodiment, a protuberance comprises a shape of a: polygon, decagon, digon, dodecagon, nonagon, henagon hendecagon, heptagon, hexadecagon, hexagon icosagon, octagon, pentagon, triangle, Penrose tile, trapezium, isosceles, trapezium undecagon, quadrilateral, Lozenge, rhomboid, rectangle, square, rhombus, trapezoid, polydrafter, arbelos, circle, disc, circle, excircle, crescent, dome, ellipse, lune, oval, sphere, asteroid, or deltoid.

In another embodiment, each protuberance 22 has a curved outer contour 26. In another embodiment, each protuberance has a different curved outer contour. In another embodiment, each protuberance 22 has a convexity.

In another embodiment, a protuberance comprises a dome shape. In another embodiment, a protuberance as described herein comprises a dome shape which further comprises multiple different convexities. In another embodiment, each protuberance 22 comprises a different convexity. In another embodiment, each protuberance 22 comprises a different set of convexities. The cross-section of the contour 26, that is, either the cross-section taken with respect to a longitudinal axis 28 (FIG. 4) of support member 12 (corresponding to the shape seen in FIG. 2) or the cross-section taken with respect to a latitudinal axis 30 (FIG. 4) of support member 12 (corresponding to the shape seen in FIG. 3), or any other cross-section, may have any curvilinear shape. Each possibility represents a separate embodiment of the present invention.

In another embodiment, the contours 26 may have the shape of a conic section, that is, the shape of a circle, ellipse, parabola or hyperbola. The various cross-sections of the contours 26 of protuberance 22 may be shaped identically or differently. In another embodiment, the shape of a protuberance is defined by equal arches. In another embodiment, the shape of a protuberance is defined by a variety of arches of different radiuses which are tangent to each other. In another embodiment, the shape of a protuberance is symmetrical. In another embodiment, the shape of a protuberance is asymmetrical. In another embodiment, a protuberance is a bulbous protuberance. Each possibility represents a separate embodiment of the present invention.

In another embodiment, the invention provides that the device such as footwear 10 supports the foot of a subject only by the two protuberances when the two protuberances are placed on a ground surface. In another embodiment, the invention provides that the device such as footwear 10 supports the foot of a subject during stance only by the two protuberances when the two protuberances are placed on a ground surface. In another embodiment, the invention provides that during stance only the 2 ground engaging surfaces of the protuberances (such as the peak or the surface facing the ground) are in contact with a ground surface. In another embodiment, the invention provides that during stance only the ground engaging surface in each protuberance is in contact with a ground surface. Each possibility represents a separate embodiment of the present invention.

In another embodiment, at least two bulbous protuberances 22 protrude from a lower surface 24 of support member 12. In another embodiment, only two bulbous protuberances 22 protrude from a lower surface 24 of support member 12. In another embodiment, a lower surface of support member is an outsole. In another embodiment, only two bulbous protuberances 22 protrude from a lower surface 24 of support member 12.

In another embodiment, the ground engaging parts of the device are only the protuberances. In another embodiment, during all phases of gait including the stance phase the protuberances are the only parts of the device which are ground engaging. In another embodiment, during all phases of gait including the stance phase the protuberances 22 are the only parts of the device which are in direct contact with the ground. Each possibility represents a separate embodiment of the present invention.

In another embodiment, a protuberance as described herein is movable. In another embodiment, a protuberance as described herein is fixed. In another embodiment, a protuberance as described herein is mountable. In another embodiment, a protuberance as described herein is replaceable. In another embodiment, a protuberance as described herein is movable along the outer surface of the support member. In another embodiment, a protuberance as described herein is movable along the outer surface of the outsole. In another embodiment, a protuberance as described herein can be positioned within the outer surface of the support member. Each possibility represents a separate embodiment of the present invention.

In another embodiment, a protuberance as described herein is movable or translatable such as in a track (e.g., forwards, backwards, sideways or diagonally) and/or rotatable about its own or other axis, or a combination of such motions. Each possibility represents a separate embodiment of the present invention.

In another embodiment, a protuberance is movable within a predefined area. In another embodiment, a protuberance is movable within an area of 1 cm$^2$ to 18 cm$^2$. In another embodiment, a protuberance is movable within an area of 1 cm$^2$ to 6 cm$^2$. In another embodiment, a protuberance is movable within an area of 1 cm$^2$ to 4 cm$^2$. In another embodiment, a protuberance is movable within an area of 2 cm$^2$ to 8 cm$^2$. In another embodiment, a protuberance is movable within an area of 3 cm$^2$ to 6 cm$^2$. In another embodiment, a protuberance is movable within an area of 4 cm$^2$ to 10 cm$^2$. In another embodiment, a protuberance is movable within an area of 5 cm$^2$ to 18 cm$^2$. In another embodiment, a protuberance is movable within an area of 4 cm$^2$ to 12 cm$^2$. Each possibility represents a separate embodiment of the present invention.

In another embodiment, a predefined area is a circle. In another embodiment, a predefined area is a square. In another embodiment, a predefined area is an ellipse. In another embodiment, a predefined area is a rectangle. In another embodiment, a predefined area is quadrangular. In another embodiment, a predefined area comprises any shape known to one of skill in the art. In another embodiment, a predefined area is shapeless. Each possibility represents a separate embodiment of the present invention.

In another embodiment, a protuberance can be positioned anywhere on the support member. In another embodiment, a protuberance can be fixed anywhere on the support member. In another embodiment, a protuberance can be positioned and/or fixed anywhere within a predefined area. In another embodiment, the protuberance is hooked to a rail. In another embodiment, the protuberance is connected to a rail. In another embodiment, the protuberance is connected to a rail and is movable along the rail. In another embodiment, the protuberance is connected to a rail, is movable along the rail, and can be positioned and/or fixed anywhere along the rail. Each possibility represents a separate embodiment of the present invention.

In another embodiment, a protuberance is slidingly mounted on support member. In another embodiment, a protuberance is mounted on a track 36 (FIG. 2) formed in the lower surface 24 of support member 12, and is selectively positioned anywhere along the track and fastened and or fixed thereto. In another embodiment, track 36 extends along a portion of the shoe sole or all along the length of the shoe sole. Alternatively or additionally, the amount of protrusion of a protuberance is adjusted, such as by mounting protuberance with a threaded fastener 38 (FIG. 3) to support member 12 and tightening or releasing threaded fastener. In another embodiment, the term "fastening", "fixing" and "securing" are used interchangeably. Each possibility represents a separate embodiment of the present invention.

Figure 3:
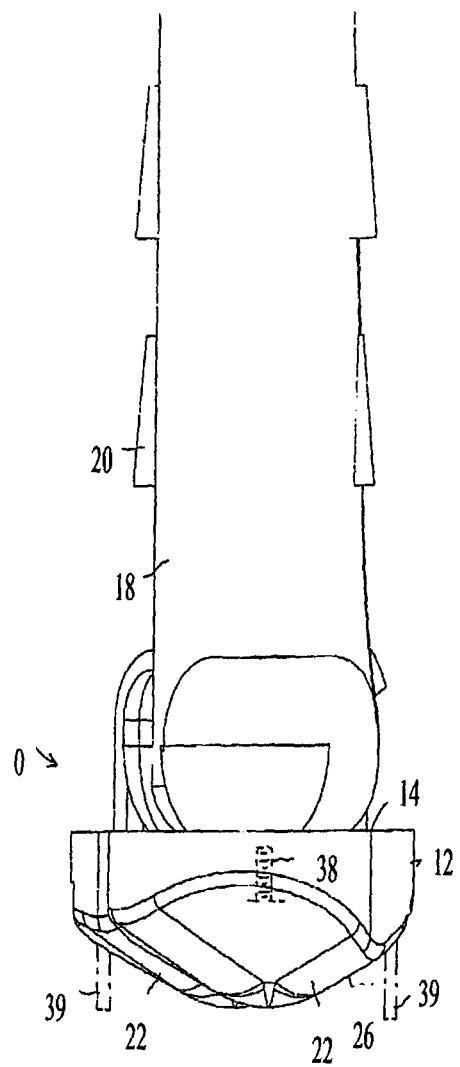

In another embodiment, a device as described herein further comprises an additional bulbous protuberance or bulbous protuberances, non-bulbous protuberance 39, or non-bulbous protuberances shown in FIG. 3. In another embodiment, protuberances 39 are formed in the shape of a peg, stud, bolt, pin, dowel and the like, although the invention is not limited to these shapes. In another embodiment, protuberances 39 may be rigid or flexible. In another embodiment, protuberances 39 are of different resilience or hardness, such as having different elasticity properties or Shore hardness. In another embodiment, protuberances 39 protrude by different amounts from the lower surface 24 of support member 12. In another embodiment, the amount of protrusion of protuberances 39 or height is adjusted. In another embodiment, protuberance 39 is fixed or movable at any place on the lower surface 24 of support member 12 Each possibility represents a separate embodiment of the present invention.

In another embodiment, a protuberance is slidingly mounted on support member 12. In another embodiment, a device such as footwear 10 comprises a sliding/shifting mechanism for a protuberance inside the sole of footwear 10. In another embodiment, the sliding/shifting mechanism comprises, without limitation, a mechanism that floats in a viscous matrix (e.g., fluid in a chamber formed in the sole), that is suspended by inner cables, or a niche trapping a protuberance with a fixing mean. Each possibility represents a separate embodiment of the present invention.

Fixing a BP

Figure 2:
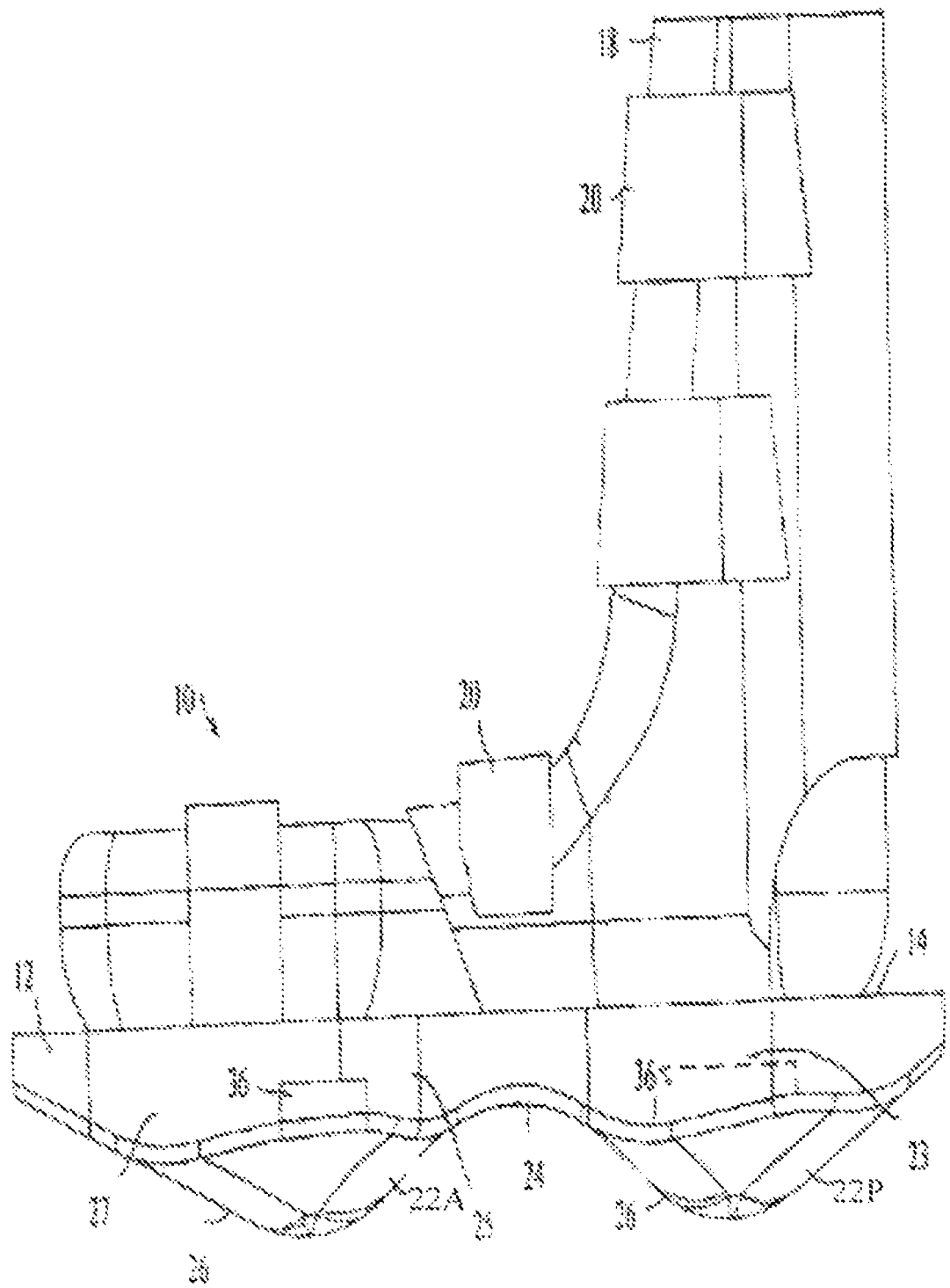
FIGS. 2 and 3 are simplified side-view and rear-view illustrations, respectively, of the footwear of FIG. 1.

As seen clearly in FIG. 2, one protuberance 22 may be positioned more posteriorly than the other protuberance 22. In another embodiment, a device as described herein comprises at least one anterior protuberance. In another embodiment, a device as described herein comprises at least one posterior protuberance. In another embodiment, the device consists one anterior protuberance and one posterior protuberance. In another embodiment, the device comprises at least one anterior protuberance and one moveable posterior protuberance. In another embodiment, the device comprises at least one moveable anterior protuberance and one posterior protuberance. In another embodiment, the device comprises at least one moveable anterior protuberance and one moveable posterior protuberance. In another embodiment, the device consists one moveable anterior protuberance and one moveable posterior protuberance. Each possibility represents a separate embodiment of the present invention.

In another embodiment, the protuberances rise vertically and therefore each protuberance comprises a base end and a peak end. In another embodiment, the surface area of the base is larger than the surface area of the peak. In another embodiment, the peak is the ground engaging portion of a protuberance in the stance phase. In another embodiment, the peak is the ground engaging portion of a protuberance in all gait phases. Each possibility represents a separate embodiment of the present invention.

In another embodiment, a protuberance such as a bulbous protuberance 22 protrudes from the upper surface 14 of support member 12.

Positions of BPs

Reference is now made, in one embodiment, to FIGS. 1-4, which illustrate footwear 10 constructed and operative in accordance with an embodiment of the present invention. Footwear 10, in one embodiment, is supplied as one or more pairs of shoe-like devices, or alternatively, as just one of the shoe-like devices. In another embodiment, a shoe-like device comprises a shoe platform and protuberances. Footwear 10, in one embodiment, is designed to adapt on a shoe such as Footwear 10. Footwear 10, in one embodiment, is a sandal or sandal-like footwear. In another embodiment, the shoe platform is a boot. In another embodiment, the shoe platform resembles a hiking boot. Each possibility represents a separate embodiment of the present invention. Each possibility represents a separate embodiment of the present invention.

In another embodiment, the footwear 10 comprises a support member 12 having a periphery in a shape of a shoe sole with an upper surface 14. In another embodiment, the footwear 10 comprises an insole placed on top of the upper surface 14. In another embodiment, the insole is the interior bottom of footwear 10. In another embodiment, the insole sits directly beneath the foot. In another embodiment, the insole is removable, replaceable, or both. In another embodiment, the insole adds comfort, control the shape, moisture, smell, or any combination thereof. In another embodiment, the insole is placed to correct defects in the natural shape of the foot or positioning of the foot during standing or walking. Each possibility represents a separate embodiment of the present invention.

In another embodiment, a support member 12 comprises an outsole. In another embodiment, a support member 12 comprises lower surface 24 or an outsole of support member 12. In another embodiment, lower surface 24 or an outsole is made of natural rubber or a synthetic imitation. In another embodiment, lower surface 24 or an outsole comprises a single piece, or may comprise separate pieces of different materials. In another embodiment, lower surface 24 or an outsole can be softer or harder. In another embodiment, a support member 12 further comprises a midsole which is a layer in between the outsole and the insole the most pressure down. In another embodiment, a support member 12 does not have a midsole. Each possibility represents a separate embodiment of the present invention.

In another embodiment, positioning at least a first bulbous protuberance and a second bulbous protuberance in a balanced position is the position in which the footwear exerts the least valgus, varus, dorsal or plantar torque about the ankle in a subject being examined. In another embodiment, positioning at least a first bulbous protuberance and a second bulbous protuberance in a balanced position is the position in which the footwear exerts the least valgus, varus, dorsal or plantar torque about the ankle in a subject being examined. In another embodiment, positioning at least a first bulbous protuberance and a second bulbous protuberance in a balanced position is the position in which the footwear provides the least or minimal lower limbs muscle activity. In another embodiment, positioning at least a first bulbous protuberance and a second bulbous protuberance in a balanced position is the position in which the footwear provides balanced lower limbs muscle activity. In another embodiment, positioning at least a first bulbous protuberance and a second bulbous protuberance in a balanced position is toning lower limb muscles. In another embodiment, positioning at least a first bulbous protuberance and a second bulbous protuberance in a balanced position is toning the amount of tension or resistance to movement in a muscle involved in gait. In another embodiment, positioning at least a first bulbous protuberance and a second bulbous protuberance in a balanced position is lower limb unloading that allows maximal ankle, knee, and hip joint mobility. In another embodiment, positioning at least a first bulbous protuberance and a second bulbous protuberance in a balanced position is providing a reduction of muscle activity, larger passive ankle excursion, improved gait ability, or any combination thereof. In another embodiment, positioning at least a first bulbous protuberance and a second bulbous protuberance in a balanced position is increasing stride length, stance symmetry, or a combination thereof. In another embodiment, positioning at least a first bulbous protuberance and a second bulbous protuberance in a balanced position is increasing the length of the force point of action in lower limb muscles such as but not limited to: soleus, tibialis posterior, and both gastrocnemius muscles. In another embodiment, positioning at least a first bulbous protuberance and a second bulbous protuberance in a balanced position is toning the plantar flexors. In another embodiment, positioning at least a first bulbous protuberance and a second bulbous protuberance in a balanced position is preventing excessive forward rotation as the body moves forward over the stationary foot. In another embodiment, positioning at least a first bulbous protuberance and a second bulbous protuberance in a balanced position is toning the push off of the heel. Each possibility represents a separate embodiment of the present invention.

Figure 4:
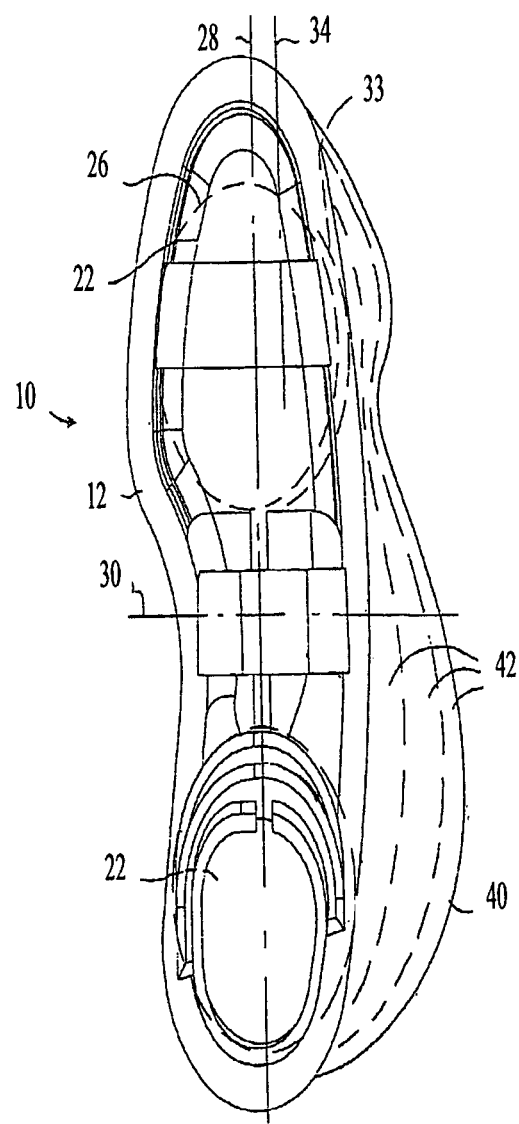
FIG. 4 is a simplified top-view illustration of the footwear of FIG. 1, showing further features of other embodiments of the present invention.

In another embodiment, as seen in FIG. 4, the protuberances are positioned on a common longitudinal axis of support member 12, such as the centerline 28 of support member 12. In another embodiment, the protuberances are positioned on opposite sides of the latitudinal midline 30. In another embodiment, the protuberances are positioned offset from the centerline 28 of support member 12, and on opposite sides of the latitudinal midline 30. In another embodiment, the bases of the protuberances are positioned on the centerline of the support member. In another embodiment, the peaks of the protuberances are positioned on opposite sides of the centerline of support member. Each possibility represents a separate embodiment of the present invention. In some embodiments, the meaning of "protuberance is positioned offset from the centerline" comprises that the peak or the ground engaging surface of a protuberances is positioned offset from the centerline. In some embodiments, the meaning of "protuberance is positioned offset from the centerline" comprises that only the peak or the ground engaging surface of a protuberances is positioned offset from the centerline but the centerline still crosses the protuberance.

In accordance with an embodiment of the present invention, footwear 10 may comprise a flange 40 that extends outwards from the periphery of support member 12. In the illustrated embodiment, flange 40 extends sideways outwards from the periphery of support member 12. Flange 40 may be provided on one side of footwear 10, as illustrated, or may be provided on both sides.

In another embodiment, the peak or the ground engaging surface of the anterior protuberance is positioned laterally from the centerline of the support member. In another embodiment, the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is aligned with centerline. In another embodiment, the peak or the ground engaging surface of the anterior protuberance is positioned medially from the centerline of the support member and the peak or the ground engaging surface of the posterior protuberance is aligned with centerline. Each possibility represents a separate embodiment of the present invention.

In another embodiment, the peak or the ground engaging surface of the posterior protuberance is positioned laterally from the centerline of the support member. In another embodiment, the peak or the ground engaging surface of the posterior protuberance is positioned medially from the centerline of the support member. In another embodiment, the peak or the ground engaging surface of the posterior protuberance is positioned laterally from the centerline of the support member and the peak or the ground engaging surface of the anterior protuberance is aligned with centerline. In another embodiment, the peak or the ground engaging surface of the posterior protuberance is positioned medially from the centerline of the support member and the peak or the ground engaging surface of the anterior protuberance is aligned with centerline. Each possibility represents a separate embodiment of the present invention.

In another embodiment, the peak or the ground engaging surface of the posterior protuberance is positioned laterally from the centerline of the support member and the peak or the ground engaging surface of the anterior protuberance is positioned medially from the centerline of the support member. In another embodiment, the peak or the ground engaging surface of the anterior protuberance is positioned laterally from the centerline of the support member and the peak or the ground engaging surface of the posterior protuberance is positioned medially from the centerline of the support member. Each possibility represents a separate embodiment of the present invention.

Figure 5:
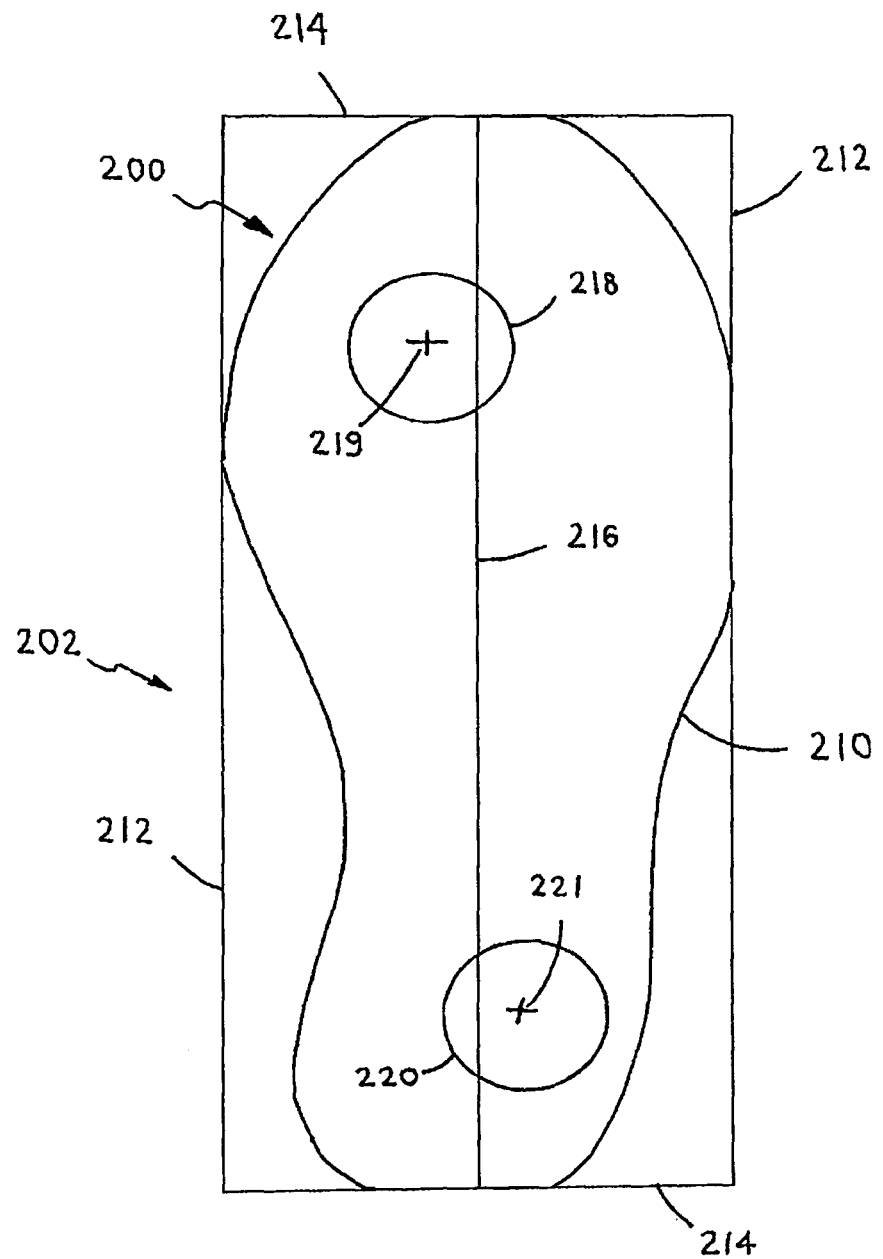
FIG. 5 is a simplified pictorial illustration of an alignment of the anterior (forward) and posterior (rearward) protuberances on a support member, according to embodiments of the present invention.
Figure 6:
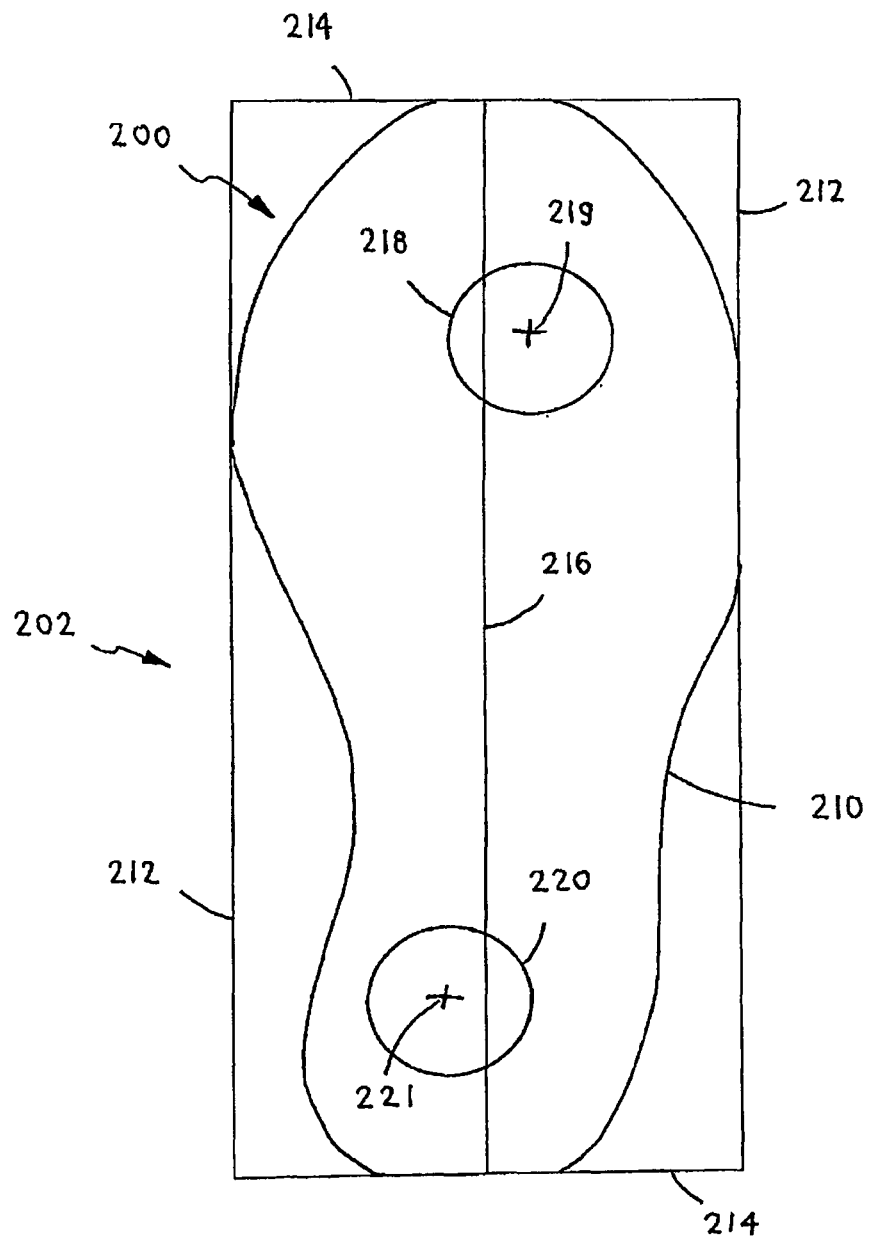
FIG. 6 is a simplified pictorial illustration of another alignment of the anterior and posterior protuberances on a support member, according to embodiments of the present invention.

In another embodiment, the centerline divides longitudinally the calcaneus support portion into two equal halves and further extends towards the phalanges and metatarsals support portion in a straight line. In another embodiment, the centerline divides longitudinally the arch of the calcaneus support portion into two equal halves and further extends towards the phalanges and metatarsals support portion in a straight line. In another embodiment, the centerline divides longitudinally the proximal arch of the calcaneus support portion into two equal halves and further extends towards the phalanges and metatarsals support portion in a straight line. In another embodiment, the centerline divides longitudinally the support portion as seen in FIGS. 5-6 of the calcaneus support portion into two equal halves and further extends towards the phalanges and metatarsals support portion in a straight line. In another embodiment of the present invention, the longitudinal centerline is defined as a longitudinal straight line connecting middles of the short sides of a rectangle which delimits a contour of the support member. Each possibility represents a separate embodiment of the present invention.

In another embodiment, the bases of the protuberances are positioned on the centerline of the support member and the peaks of the protuberances are positioned on opposite sides of the centerline of support member. In another embodiment, the bases of the protuberances are positioned on the centerline of the support member but the peaks of the protuberances are offset from the centerline of the support member. In another embodiment, the bases of the protuberances are positioned on the centerline of the support member but the peaks of the protuberances are positioned on opposite sides of the centerline of the support member. In another embodiment, positioning a protuberance is positioning the peak or the ground engaging surface of a protuberance. In another embodiment, the terms "peak" and "ground engaging surface" are used interchangeably. Each possibility represents a separate embodiment of the present invention.

In another embodiment, the anterior protuberance is positioned medially from the centerline of the support member. In another embodiment, the peak of the anterior protuberance is positioned medially from the centerline of the support member. In another embodiment, the base of the anterior protuberance is position on the centerline of the support member but the peak of the anterior protuberance is positioned medially from the centerline of the support member. In another embodiment, the anterior protuberance is positioned laterally from the centerline of the support member. In another embodiment, the peak of the anterior protuberance is positioned laterally from the centerline of the support member. In another embodiment, the base of the anterior protuberance is position on the centerline of the support member but the peak of the anterior protuberance is positioned laterally from the centerline of the support member. In another embodiment, the posterior protuberance is positioned medially from the centerline of the support member. In another embodiment, the peak of the posterior protuberance is positioned medially from the centerline of the support member. In another embodiment, the base of the posterior protuberance is position on the centerline of the support member but the peak of the posterior protuberance is positioned medially from the centerline of the support member. In another embodiment, the posterior protuberance is positioned laterally from the centerline of the support member. In another embodiment, the peak of the posterior protuberance is positioned laterally from the centerline of the support member. In another embodiment, the base of the posterior protuberance is position on the centerline of the support member but the peak of the posterior protuberance is positioned laterally from the centerline of the support member.

In another embodiment, as seen in FIG. 2, the posterior protuberance 22P is positioned generally underneath a calcaneus (heel, ankle) support portion 23 of support member 12. In another embodiment, the anterior protuberance 22A may be positioned generally underneath a metatarsals support portion 25 and/or phalanges support portion 27 of support member 12. Each possibility represents a separate embodiment of the present invention.

In another embodiment, as indicated by broken lines 33 in FIG. 4, the anterior protuberances 22A is aligned on a longitudinal axis with its peak offset from centerline 28, and the posterior protuberance 22P is also is aligned on a longitudinal axis with its peak offset from centerline 28 but to the opposite direction of 22A with respect to centerline 28. Each possibility represents a separate embodiment of the present invention.

Figure 12:
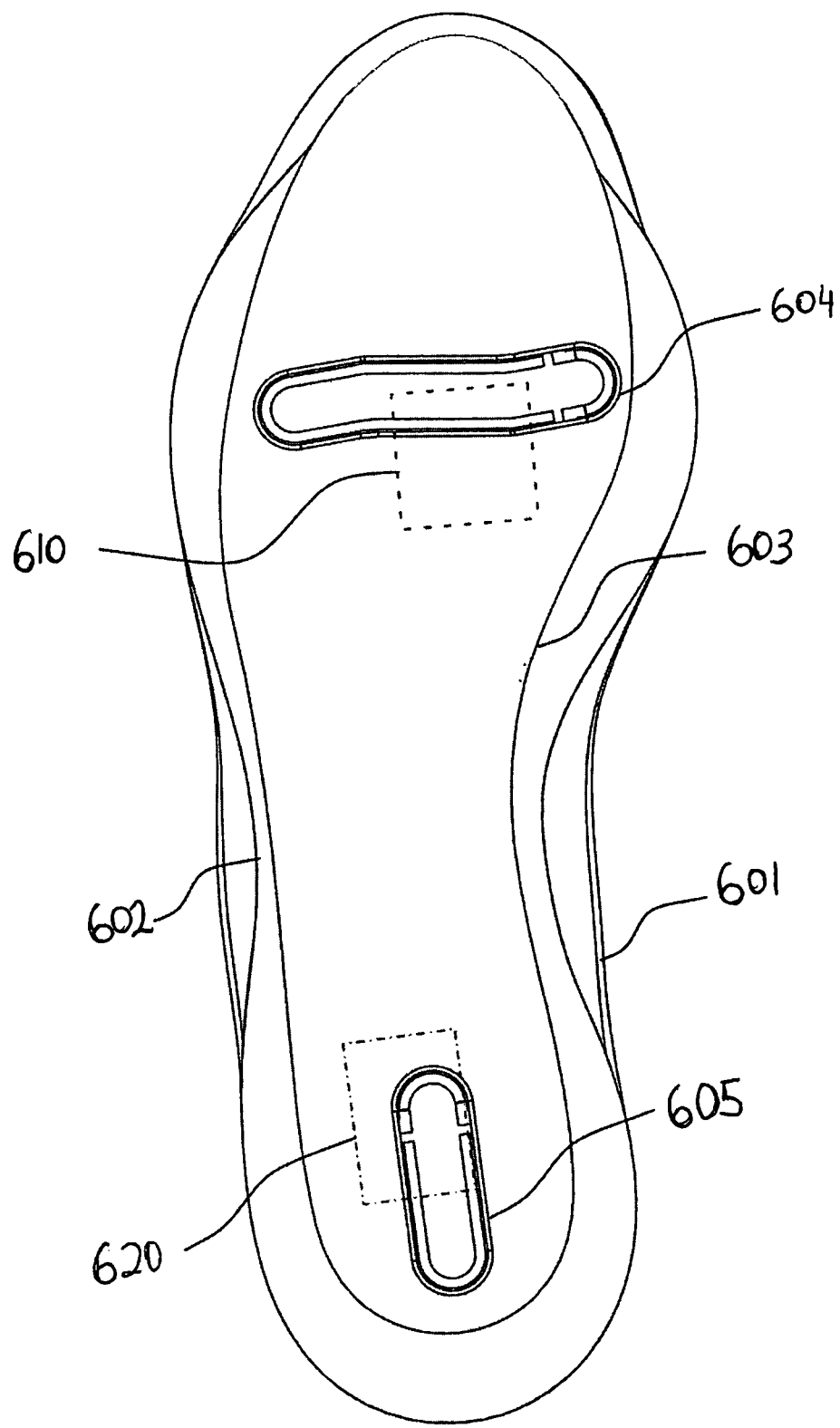
FIG. 12 illustrates effective area boundaries of positioning of the anterior and posterior protuberances with respect to a support surface, according to certain diseases of the present invention.

In another embodiment, FIG. 5 is a simplified pictorial illustration of an alignment of the anterior (forward) and posterior (rearward) protuberances on a support member 200, according to embodiments of the present invention. Centerline 216, in the embodiment shown in FIG. 12 is defined as a longitudinal straight line (median) that connects the middles of short sides 214 of a rectangle 212, the long sides 212 of which are parallel to centerline 216, and which delimits the contour 210 of the support member. In embodiments of the present invention contour 210 is the contour (254, see FIG. 7) of the foothold confined by the upper part (253, see FIG. 7) of the footwear (250, see FIG. 7), corresponding to the last which is used to form the footwear. In other embodiments of the present invention contour 210 is the outermost contour of the footwear. In other embodiments of the present invention contour 210 is the contour of the bottom surface of the sole of the footwear. In some embodiments, the terms "forward" and "anterior" are used interchangeably. In some embodiments, the terms "rearward" and "posterior" are used interchangeably. Each possibility represents a separate embodiment of the present invention.

According to embodiments of the present invention, as shown in FIG. 5, forward protuberance 218 at the anterior (phalanges) portion of the support member (i.e. its front portion) is positioned medially offset to centerline 216. By "medially offset" is meant that a peak surface (which can be the ground engaging surface) of protuberance 218 (marked by cross 219) is shifted from centerline 216 medially towards the inner side of support surface 200, facing the support member of the other foot (not shown in this figure). The peak surface is a surface on the protuberance which is furthest from the support surface with respect to other surfaces of the protuberance. Each possibility represents a separate embodiment of the present invention.

According to embodiments of the present invention, as shown in FIG. 5, rearward protuberance 220 at the posterior (calcaneus) portion of the support member (i.e. its back portion) is positioned laterally offset to centerline 216. By "laterally offset" is meant that a peak surface (which can be the ground engaging surface) of protuberance 220 (marked by cross 221) is shifted from centerline 216 laterally towards the outer side of support surface 200, away from the support member of the other foot (not shown in this figure). Each possibility represents a separate embodiment of the present invention.

The alignment of the protuberances shown in FIG. 5 is useful, for example, for exercising users with one or more of the following medical indications: medial compartment—knee osteoarthritis medial meniscus tear or damage, genu varus, patello-femoral pain syndrome, patello-femoral problem (malalignment), lateral collateral ligamental damage or tear, bone bruise MTP/MFC (AVN), low back pain, hip OA, hip labrum damage (TCM), trochanteric bursitis, pes anseninus bursitis, ankle instability (supination), achilles tendonitis and metatrsalgia. Each possibility represents a separate embodiment of the present invention.

FIG. 6 is a simplified pictorial illustration of another alignment of the anterior and posterior protuberances on a support member, according to embodiments of the present invention. According to embodiments of the present invention, as shown in FIG. 6, forward protuberance 218 is laterally offset to centerline 216, whereas rearward protuberance 220 is medially offset to centerline 216. The alignment of the protuberances shown in FIG. 5 is useful, for example, for exercising users with one or more of the following medical indications: lateral meniscus tear or damage, lateral compartment knee osteoarthritis, valgus knee (genu valgus), patello-femoral pain syndrome, patello-femoral problem (malalignment), MCL Ligament tear, bone bruise LTP/LFC (AVN), hip labrum damage or tear, hip pain, ankle instability (pronoation), achilles tendonitis, tibilias insufficiency or dysfunction and metatarsalgia. Each possibility represents a separate embodiment of the present invention.

Figure 7:
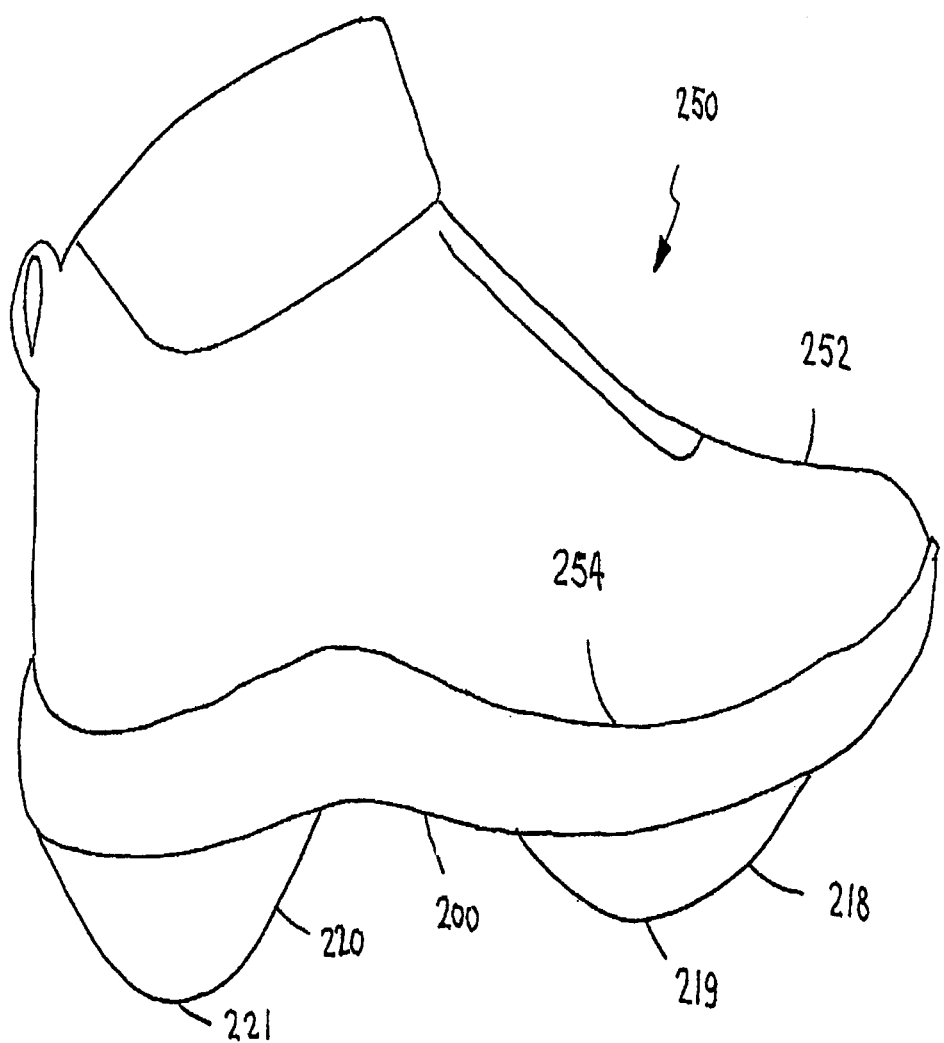
FIG. 7 is a simplified pictorial illustration of a sneaker constructed and operative in accordance with an embodiment of the present invention, whose rearward protuberance has a greater height than the height of the forward protuberance.

FIG. 7 is a simplified pictorial illustration of a sneaker 250 constructed and operative in accordance with an embodiment of the present invention, whose rearward protuberance 220 has a greater height than the height of the forward protuberance 218. It is noticeable that such arrangement facilitates initial contact between rearward protuberance 220 and the supporting ground (not shown in this figure) when a user wears the sneaker, before the forward protuberance is brought in contact with the ground. When both protuberances are placed in contact with the ground the foot of the user wearing sneaker 250 acquires a downward inclination with respect to direction of gait of the user. Each possibility represents a separate embodiment of the present invention.

Figure 8:
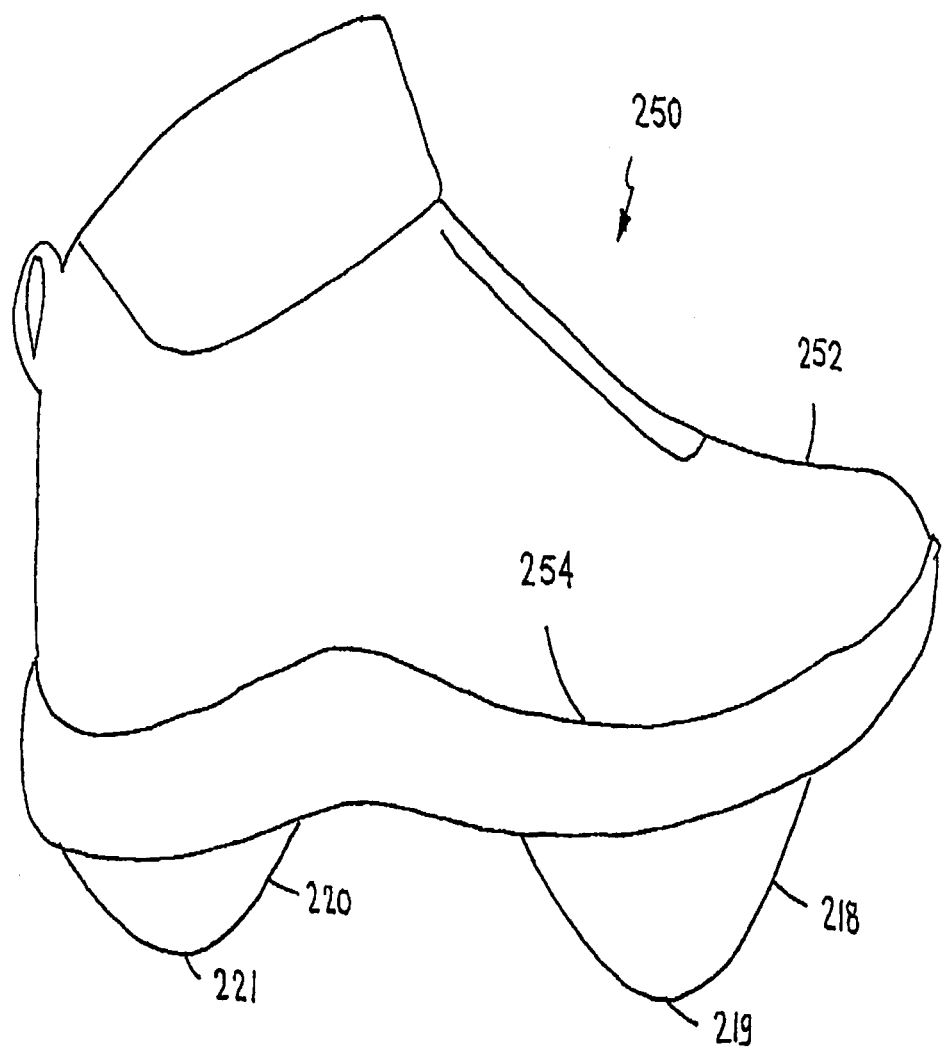
FIG. 8 is a simplified pictorial illustration of a sneaker constructed and operative in accordance with an embodiment of the present invention, whose forward protuberance has a greater height than the height of the rearward protuberance.

FIG. 8 is a simplified pictorial illustration of a sneaker 250 constructed and operative in accordance with an embodiment of the present invention, whose forward protuberance 218 has a greater height than the height of the rearward protuberance 220. In this embodiment when both protuberances are placed in contact with the ground the foot of the user wearing sneaker 250 acquires an upward inclination (with respect to the direction of gait of the user. Each possibility represents a separate embodiment of the present invention.

Figure 9:
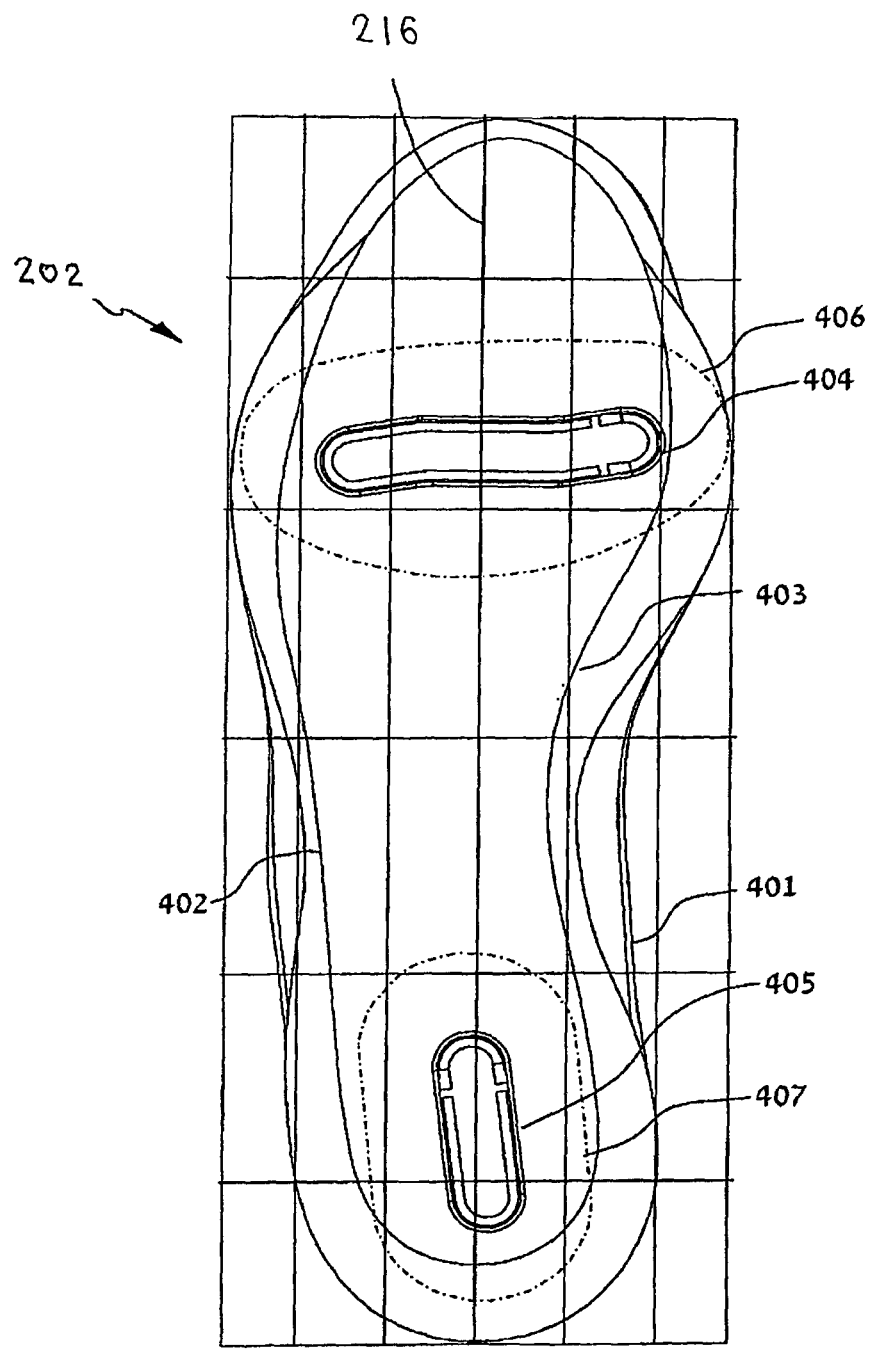
FIG. 9 illustrates maximal area boundaries of positioning of the anterior and posterior protuberances with respect to a support surface, according to embodiments of the present invention.

FIG. 9 illustrates maximal area boundaries of positioning of the anterior and posterior protuberances with respect to a support surface, according to embodiments of the present invention. Shown in this figure is a bottom view of a sneaker designed to be worn on a right foot of a user. The medial side is thus the right side of the drawing, facing the arc of greater curvature of the side arcs of the sneaker. The lateral side is opposite to the medial side that is the left side of the drawing, facing the arc of lesser curvature of the side arcs of the sneaker. Indicated are the midsole 401 and last/shoe 402, contour 403 of the foothold which is determined by the last used in the making of the sneaker. Front rail 404 and rear rail 405 are used for anchoring the protuberance. The area bordered by dotted line 406 marks the maximal area within which the peak surface of the anterior protuberance, i.e. the ground engaging surface of the anterior protuberance, may be located, according to some embodiments of the present invention. The area bordered by dotted line 407 marks the maximal area within which the peak surface of the posterior protuberance. Each possibility represents a separate embodiment of the present invention.

Figure 10:
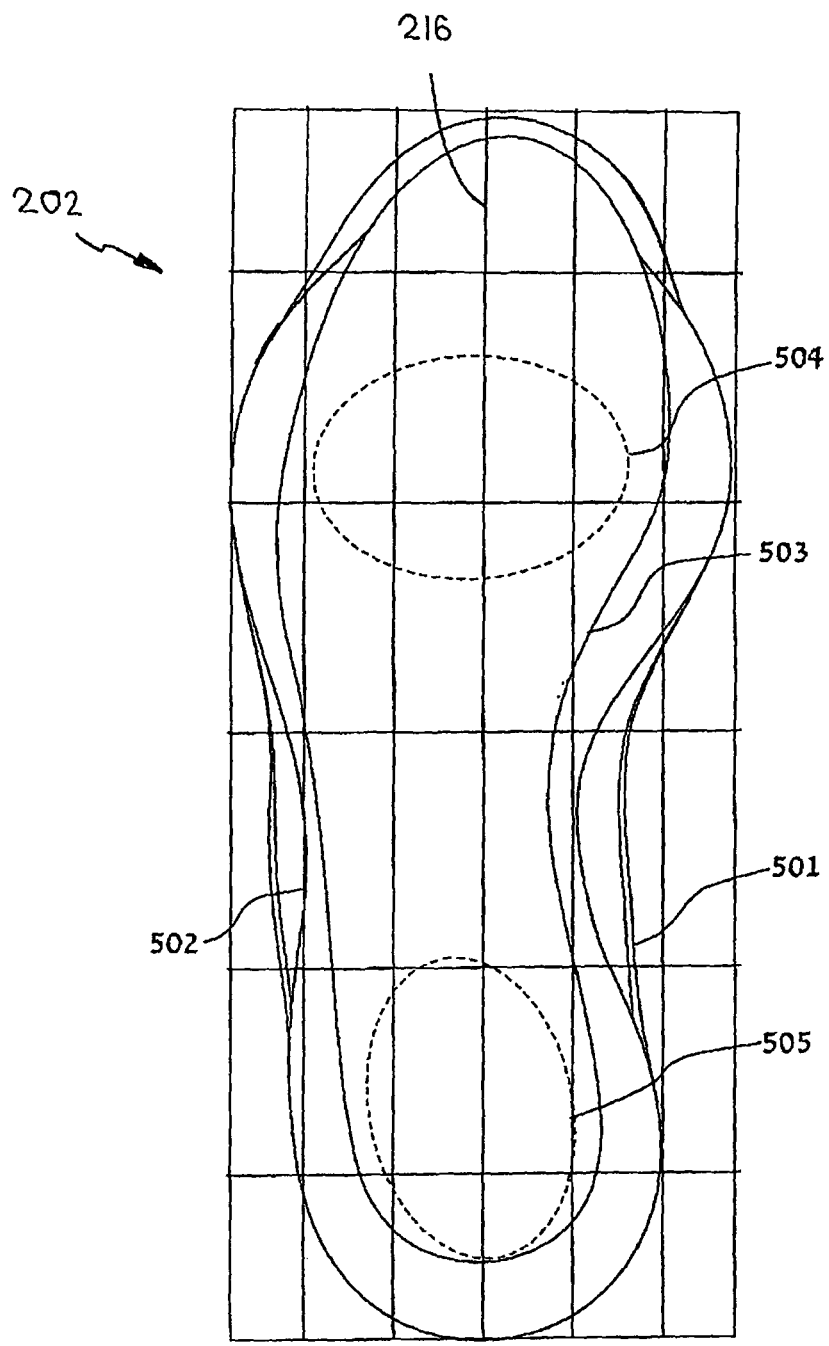
FIG. 10 illustrates effective area boundaries of positioning of the anterior and posterior protuberances with respect to a support surface, according to embodiments of the present invention.

FIG. 10 illustrates the effective area boundaries of positioning of the anterior and posterior protuberances with respect to a support surface, according to embodiments of the present invention. Indicated are the midsole 501 and outsole 502, contour 503 of the foothold which is determined by the last used in the making of the sneaker. The area bordered by dotted line 504 marks the effective area within which the peak surface of the anterior protuberance, i.e. the ground engaging surface of the anterior protuberance, may be located, according to some embodiments of the present invention. The area bordered by dotted line 505 marks the effective area within which the peak surface of the posterior protuberance. "Effective" refers to the effectiveness of use of the footwear according to embodiments of the present invention, which facilitates treatment. For clarity both FIGS. 9 and 10 are divided to 36 equal parts. The effective locations will be within the same parts regardless of sizing. Each possibility represents a separate embodiment of the present invention.

Figure 11:
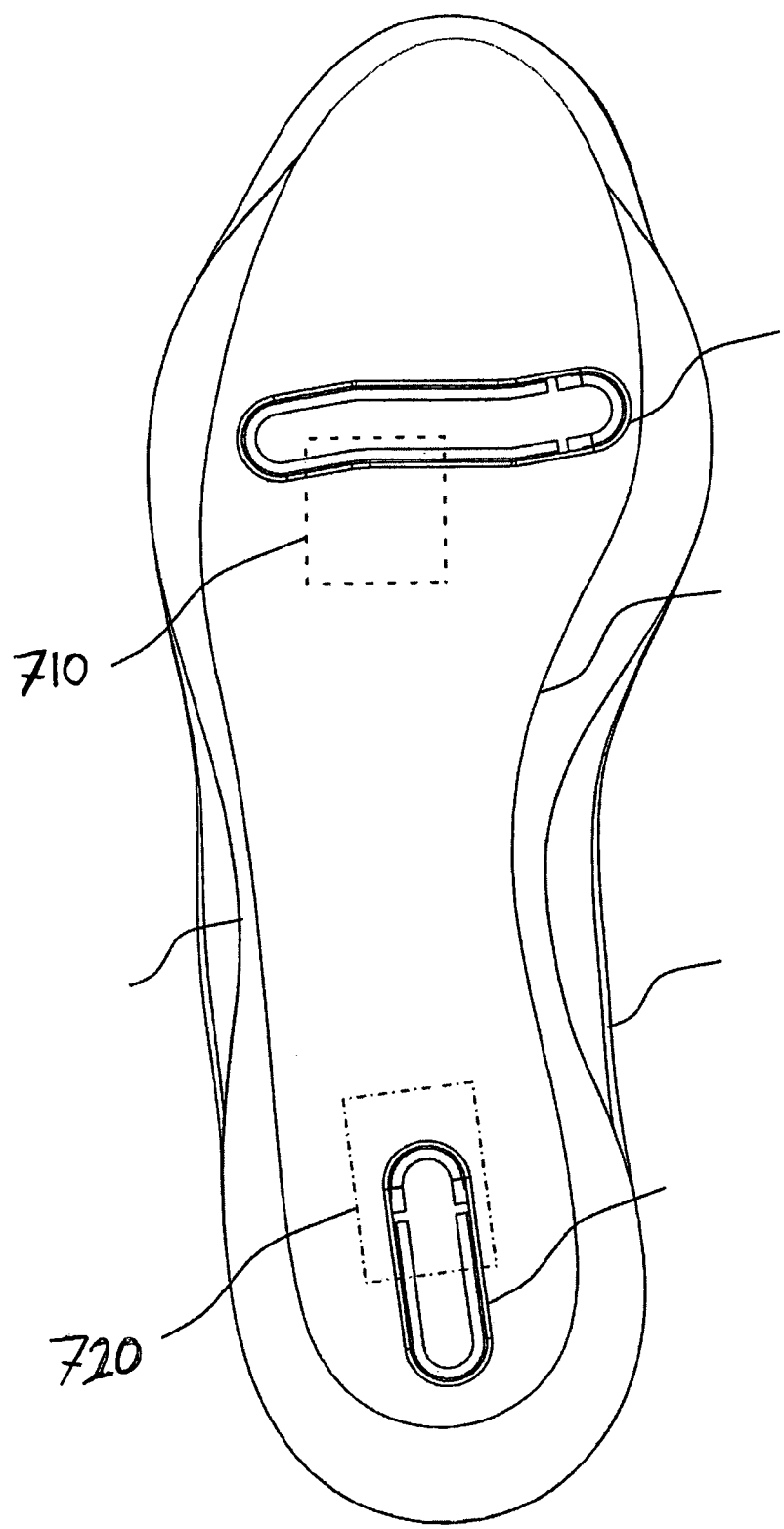
FIG. 11 illustrates effective area boundaries of positioning of the anterior and posterior protuberances with respect to a support surface, according to certain diseases of the present invention.

FIG. 11 illustrates the effective area boundaries of positioning of the anterior and posterior protuberances with respect to a support surface, according to embodiments of the present invention which include treatment and alleviating pain for the following diseases and/or conditions: Lateral meniscus tear/damage, Lateral compartment knee osteoarthritis, Valgus knee (genu valgus), Patello-femoral pain syndrome, Patello-femoral defeciency (mal-alignment), MCL Ligament tear, Bone bruise LTP/LFC (AVN), Hip labrum damage (tear), hip musculoskeletal pain, ankle instability (Pronoation), Achilles tendonitis, Tibilias insufficiency, Metatansalgia, or any combinations thereof. Indicated is the area bordered by dotted line 710 which marks the effective area within which the peak surface of the anterior protuberance, i.e. the ground engaging surface of the anterior protuberance, may be located, while treating or alleviating pain for the diseases and/or conditions described for FIG. 11 hereinabove. Indicated is the area bordered by dotted line 720 which marks the effective area within which the peak surface of the posterior protuberance, i.e. the ground engaging surface of the posterior protuberance, may be located, while treating or alleviating pain for the diseases and/or conditions described for FIG. 11 hereinabove. The areas bordered by dotted lines 710 and 720 are within the areas bordered by dotted lines 504 and 505, respectively, in FIG. 10. As provided before, FIG. 10 is divided to 36 equal parts. The effective locations will be within these effective parts regardless of sizing. Each possibility represents a separate embodiment of the present invention.

FIG. 12 illustrates the effective area boundaries of positioning of the anterior and posterior protuberances with respect to a support surface, according to embodiments of the present invention which include treatment and alleviating pain for the following diseases and/or conditions: Medial Compartment knee OA, medial meniscus—tear/damage, Genu varus, Patello-femoral pain syndrome, Patello-femoral problem (malalignment), Lateral collateral ligamental (damage/tear), Bone bruise MTP/MFC (AVN), hip OA, Hip labrum damage (TCM), Trochanteric bursitis, Pes Ansenius bursitis, Ankle instability (supination+ext rut), Achilles tendonitis, Metatrsalgia, or a combination thereof. Indicated are the midsole 601 and outsole 602, last 603 of the foothold which is determined by the last used in the making of the sneaker. Front rail 604 and rear rail 605 are used for anchoring the protuberance. Indicated is the area bordered by dotted line 610 which marks the effective area within which the peak surface of the anterior protuberance, i.e. the ground engaging surface of the anterior protuberance, may be located, while treating or alleviating pain for the diseases and/or conditions described for FIG. 12 hereinabove. Indicated is the area bordered by dotted line 620 which marks the effective area within which the peak surface of the posterior protuberance, i.e. the ground engaging surface of the posterior protuberance, may be located, while treating or alleviating pain for the diseases and/or conditions described for FIG. 12 hereinabove. The areas bordered by dotted lines 610 and 620 are within the areas bordered by dotted lines 504 and 505, respectively, in FIG. 10. As provided before, FIG. 10 is divided to 36 equal parts. The effective locations will be within these effective parts regardless of sizing. Each possibility represents a separate embodiment of the present invention.

Figure 13A:
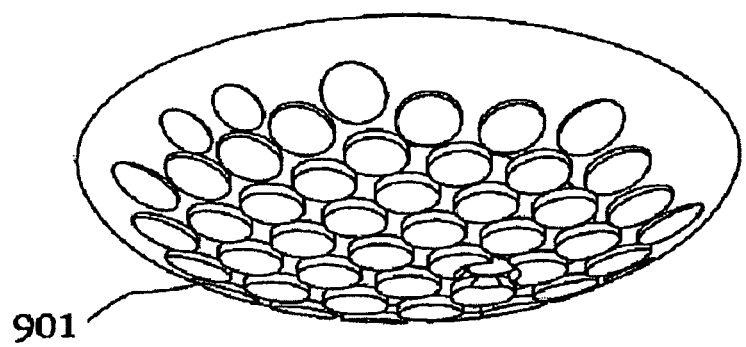
FIG. 13A is an isometric view of a protuberance suitable for use on a footwear, according to embodiments of the present invention.

FIG. 13A is an isometric view of a protuberance suitable for use on a footwear, according to embodiments of the present invention. Cleats 901, according to embodiments of the present invention, cover the ground engaging area of a protuberance, for facilitating enhanced grip of the surface on which the user stands or walks. FIG. 18B is a frontal view of a protuberance suitable for use on a footwear, according to embodiments of the present invention. The peak surface is marked by cross 902. Bore 904 is provided for a screw or other fastening arrangement to fix the protuberance in the desired position. FIG. 18C is a side view of a protuberance suitable for use on a footwear, according to embodiments of the present invention. Convexity 905 of the protuberance is clearly seen. Various convexities may be employed, all of which define a peak surface, typically (but not necessarily) at the center of the protuberance, which is the surface which comes in contact with the ground, when the user attaches the support member to the foot, and walks or stands on the ground.

Figure 13B:
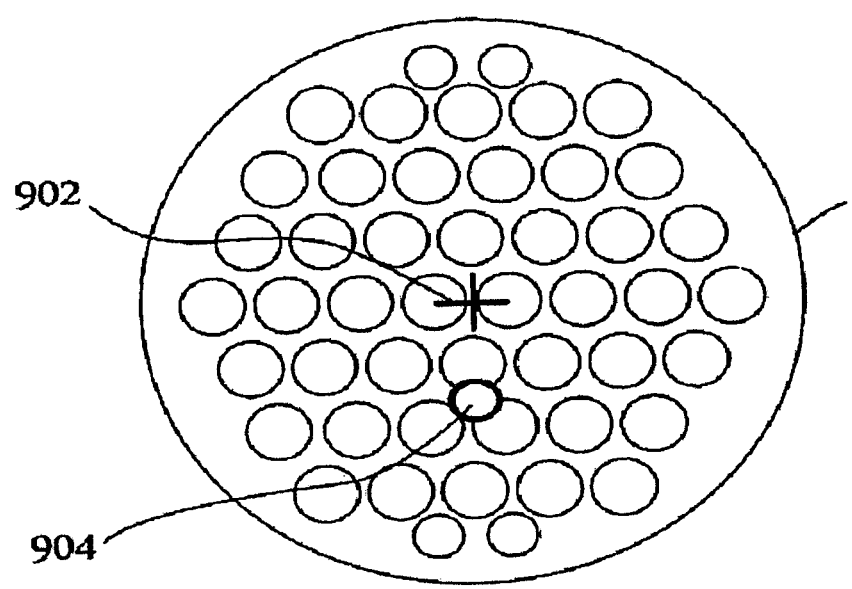
FIG. 13B is a frontal view of a protuberance suitable for use on a footwear, according to embodiments of the present invention.
Figure 13C:
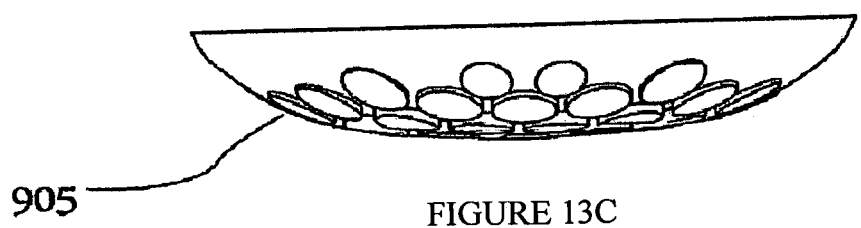
FIG. 13C is a side view of a protuberance suitable for use on a footwear, according to embodiments of the present invention.

FIG. 13 is a simplified pictorial illustration of a protuberance according to embodiments of the present invention. As shown a protuberance is convex 905 (13C). Each protuberance, according to embodiments of the present invention, comprises a fixing hole (for fixing a protuberance) 904 in which a latch, a bolt, or a screw is placed therein. The peak of a protuberance, which in some embodiments of the present invention, is placed within the center of the ground engaging area 902 is in contact with the ground during stance (13B). A grip structure 901, Resilience, Hardness, Size, Weight and Elasticity In another embodiment, calibrating comprises positioning a protuberance on a support member. In another embodiment, calibrating comprises adjusting the height or protrusion of a protuberance. In another embodiment, calibrating comprises adjusting a resilience of a protuberance. In another embodiment, calibrating comprises adjusting a hardness of a protuberance. In another embodiment, calibrating comprises adjusting an elasticity of a protuberance. Each possibility represents a separate embodiment of the present invention.

In another embodiment, a protuberance is compressible. In another embodiment, a protuberance is deformable. In another embodiment, a protuberance is compressible or deformable upon pressure exerted by subject's weight. Each possibility represents a separate embodiment of the present invention.

In another embodiment, a protuberances is constructed of any suitable material, such as but not limited to, elastomers or metal or a combination of materials, and have different properties. In another embodiment, a protuberance comprises different resilience or hardness, such as having different elasticity properties or Shore hardness. Each possibility represents a separate embodiment of the present invention.

In another embodiment, a protuberance comprises spikes or grip means for providing better stability. In another embodiment, a protuberance comprises spikes or grip means as anti-slippery means. In another embodiment, FIG. 13 provides a protuberance comprising small rounded grip means. In another embodiment, spikes or grip means are constructed of any suitable material, such as but not limited to: elastomers such as rubbers or plastic materials. In another embodiment, spikes or grip means cover only a portion of a protuberance. In another embodiment, spikes or grip means cover at least a ground engaging surface of a protuberance (the surface in contact with the ground during stance). In another embodiment, a fixing means for securing a protuberance to the support portion is embedded within a spikes or a grip means. In another embodiment, a fixing means for securing a protuberance to the support portion is places in between spikes or a grip means. Each possibility represents a separate embodiment of the present invention.

In another embodiment, a protuberance has a shore hardness of between 30 to 90 Sh A. In another embodiment, a protuberance has a shore hardness of between 40 to 55 Sh A. In another embodiment, a protuberance has a shore hardness of between 50 to 70 Sh A. In another embodiment, a protuberance has a shore hardness of between 65 to 90 Sh A. In another embodiment, a protuberance has a shore hardness of between 55 to 60 Sh A. In another embodiment, a protuberance has a shore hardness of between 65 to 70 Sh A. In another embodiment, an anterior and a posterior protuberance comprise identical shore hardness. In another embodiment, an anterior and a posterior protuberance comprise different shore hardness. Each possibility represents a separate embodiment of the present invention.

In another embodiment, a protuberance is a soft protuberance comprising a shore hardness of between 40 to 55 Sh A. In another embodiment, a protuberance is a medium hardness protuberance comprising a shore hardness of between 50 to 70 Sh A. In another embodiment, a protuberance is a hard protuberance comprising a shore hardness of between 65 to 90 Sh A.

In another embodiment, a protuberance has an abrasion between 1-60 mm$^3$ (by DIN 53516). In another embodiment, a protuberance comprises a rubber cup. In another embodiment, a protuberance comprises natural rubber compounds. In another embodiment, a protuberance comprises synthetic rubber compounds such as TPU or TPR. In another embodiment, a protuberance comprises silicone. In another embodiment, a protuberance a plastic material such as PA 6 (nylon), PA6/6 (nylon)+glass fiber, ABS, Polypropylene, POM (Polyoxymethylene). In another embodiment, a protuberance comprises a metal such as aluminum, steel, stainless steel, brass, or metal alloys. In another embodiment, a protuberance comprises compound materials such as glass fibers, carbon fibers, kevlar, or any combination thereof. Each possibility represents a separate embodiment of the present invention.

In another embodiment, different heights of a protuberance can be used. In another embodiment, height is calibrated by adding a spacer between a protuberance and the outsole. In another embodiment, different weights of a protuberance can be used. In another embodiment, weight is calibrated by adding a spacer between a protuberance and the outsole.

In another embodiment, the height of the anterior protuberance differs from the height of the posterior protuberance. In another embodiment, the height of the anterior protuberance or of the posterior protuberance is adjusted with round spacers positioned between the support member or the outsole and the base portion of a protuberance. In another embodiment, a spacer is fixed between the outsole and base portion of a protuberance. Each possibility represents a separate embodiment of the present invention.

In another embodiment, a spacer or a protuberance comprises a diameter of 50-150 mm. In another embodiment, a spacer or a protuberance comprises a diameter of 55-110 mm. In another embodiment, a spacer or a protuberance comprises a diameter of 60-100 mm. In another embodiment, a spacer or a protuberance comprises a diameter of 80-90 mm. In another embodiment, a spacer or a protuberance comprises a diameter of 85 mm. In another embodiment, a spacer or a protuberance or a protuberance comprises a thickness of 1-12 mm. In another embodiment, a spacer or a protuberance comprises a thickness of 1-4 mm. In another embodiment, a spacer or a protuberance comprises a thickness of 3-10 mm. In another embodiment, a spacer or a protuberance comprises a thickness of 1-3 mm. In another embodiment, a spacer or a protuberance comprises hardness of 60-70 Shore A, which is a soft spacer. In another embodiment, a spacer or a protuberance comprises hardness of 90-100 Shore A, which is a hard spacer. In another embodiment, a spacer or a protuberance comprises hardness of 71-890 Shore A, which is medium hardness spacer.

In another embodiment, a spacer or a protuberance weighs 2-500 g. In another embodiment, a spacer or a protuberance weighs 2-250 g. In another embodiment, a spacer or a protuberance weighs 2-6 g. In another embodiment, a spacer or a protuberance weighs 2-20 g. In another embodiment, a spacer or a protuberance weighs 2-20 g is made of Nylon. In another embodiment, a spacer or a protuberance weighs 2-20 g is made of Nylon and fiber. In another embodiment, a spacer or a protuberance weighs 2-40 g is made of Nylon and glass fiber. In another embodiment, a spacer or a protuberance weighs 30-100 g. In another embodiment, a spacer or a protuberance weighs 50-80 g. In another embodiment, a spacer or a protuberance weighs 60-100 g. In another embodiment, a spacer or a protuberance comprises: Nylon glass fiber polyurethane an alloy (such as but not limited to Zink alloy), or any combination thereof. Each possibility represents a separate embodiment of the present invention.

Adjustments of the Device's Protuberances to Treat Diseases/Pathologies/Pain

In another embodiment, a device or footwear 10 is secured to a subject afflicted with patella-femoral pain and hyper-laxity, immediately the posterior protuberance and the anterior protuberance are calibrated or positioned in a balanced position; then the posterior protuberance and the anterior protuberance were further calibrated or adjusted in a minimal pain position. Each possibility represents a separate embodiment of the present invention.

In another embodiment, a device or footwear 10 is secured to a subject afflicted with patella-femoral pain, an early heel rise, and hyper-laxity, immediately the posterior protuberance and the anterior protuberance are calibrated or positioned in a balanced position; then the posterior protuberance and the anterior protuberance were further calibrated or adjusted in a minimal pain position; then the height of posterior protuberance was increased (such that the posterior protuberance was higher than anterior protuberance) in order to reduce an early heel rise. Each possibility represents a separate embodiment of the present invention.

In another embodiment, a device or footwear 10 is secured to a subject afflicted with patella-femoral knee OA, a relative higher ROM (range of motion) of knee compare to age matched, pain that is relieved upon walking up-hill, and a delayed heel rise, immediately the posterior protuberance and the anterior protuberance are calibrated or positioned in a balanced position; then the posterior protuberance and the anterior protuberance were further calibrated or adjusted in a minimal pain position; then the height of the anterior protuberance was increased in order adjust subject's heel rise during stance. Each possibility represents a separate embodiment of the present invention.

In another embodiment, a device or footwear 10 is secured to a subject afflicted with medial compartment knee OA, a sudden strong pain in the left knee, an A-vascular necrosis in the proximal medial tibia plateau of the left knee, a single limb support of 33% in the left leg, and a single limb support of 37.5% in the right leg, immediately the posterior protuberance and the anterior protuberance were calibrated or positioned in a balanced position; then the posterior protuberance and the anterior protuberance were further calibrated or adjusted in a minimal pain position; then the height of the anterior protuberance and the height of the posterior protuberance was increased under the left leg. Each possibility represents a separate embodiment of the present invention.

In another embodiment, a device or footwear 10 is secured to a subject afflicted with knee pain during heel-strike and calibration comprised positioning the posterior protuberance laterally to the centerline. In another embodiment, a device or footwear 10 is secured to a subject afflicted with knee pain during mid-stance/toe-off and calibration comprised positioning the anterior protuberance laterally to the centerline. Each possibility represents a separate embodiment of the present invention.

In another embodiment, a device or footwear 10 is secured to a subject afflicted with pain in the pes anserinus region during heel-strike and calibration comprised positioning the posterior protuberance medially to the centerline. In another embodiment, a device or footwear 10 is secured to a subject afflicted with pain in the pes anserinus region during Mid-stance/Toe-off and calibration comprised positioning the anterior protuberance medially to the centerline. Each possibility represents a separate embodiment of the present invention.

In another embodiment, a device or footwear 10 is secured to a subject afflicted with pain in the medial aspect of patella during heel-strike and calibration comprised positioning the posterior protuberance anteriorly (forward) towards the latitude. In another embodiment, a device or footwear 10 is secured to a subject afflicted with pain in the medial aspect of patella during Mid-stance/Toe-off and calibration comprised positioning the anterior protuberance posteriorly towards the posterior end of the calcaneus support portion. Each possibility represents a separate embodiment of the present invention.

In another embodiment, a device or footwear 10 is secured to a subject afflicted with pain in the lateral aspect of patella during heel-strike and calibration comprised positioning the posterior protuberance anteriorly (forward). In another embodiment, a device or footwear 10 is secured to a subject afflicted with pain in the lateral aspect of patella during Mid-stance/Toe-off and calibration comprised positioning the anterior protuberance posteriorly to the centerline. Each possibility represents a separate embodiment of the present invention.

In another embodiment, a device or footwear 10 is secured to a subject afflicted with pain in the supra patellar region during heel-strike and calibration comprised positioning the posterior protuberance anteriorly (forward). In another embodiment, a device or footwear is secured to a subject afflicted with pain in the supra patellar region during Mid-stance/Toe-off and calibration comprised positioning the anterior protuberance posteriorly to the centerline. Each possibility represents a separate embodiment of the present invention.

In another embodiment, a device or footwear 10 alleviates pain in the medial femoral condyle region. In another embodiment, a device or footwear 10 alleviates pain during heel-strike. In another embodiment, a device or footwear 10 alleviates pain during mid-stance/Toe-off. In another embodiment, a device or footwear 10 alleviates pain in the medial femoral condyle region. In another embodiment, a device or footwear 10 alleviates pain in the medial proximal aspect of tibia region. In another embodiment, a device or footwear 10 alleviates pain in the lateral proximal aspect of tibia region. In another embodiment, a device or footwear 10 alleviates pain in the region of insertion of medial head of gastrocnemious. In another embodiment, a device or footwear 10 alleviates pain in the region of insertion of the Achilles tendon. In another embodiment, a device or footwear alleviates pain in the region of insertion of medial hamstring. In another embodiment, a device or footwear 10 alleviates pain in the region of insertion of lateral hamstring. In another embodiment, a device or footwear 10 alleviates pain in the region of insertion of lateral head of gastrocnemious. Each possibility represents a separate embodiment of the present invention.

In another embodiment, a lower limb musculoskeletal pain or disorder such as described herein creates a gait disorder that is treatable according to the methods described herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Pain Scale

In all case studies pain is presented as graded by the patient on a 10 cm Visual analogue scale. A pain of 4/10 means 4 cm out of 10 cm (where "0" is no pain and "10" is the worst pain).

Positioning Method

After each change (calibration, positioning, and finally securing/fastening) in configuration of the protuberances attached to the footwear, the patient was asked to walk a distance of 10 meters away from the therapist and then back in order to verify that the patient remains balanced and that the change in configuration resulted in a desired positive effect (i.e. reduction in pain, improvement of timing of the heel-rise etc').

Prescribing the Device

The device comprises 2 units of footwear: one for the left foot and one to the right foot. The footwear used is a light walking boot.

Prescription included a set of instructions to the patients. These instructions included: the length of wear the device per day (usually 30-60 minutes daily). Daily use included wearing the device during routine activities that may include watching TV, computer activities; eating activities, etc. Actual walking constituted 10-25% of 30-60 minutes. Thus, if patient worn the device for 60 minutes per day, total of 5-10 minutes were dedicated, accumulatively, to walking.

Example 1: Treating a Bi-Lateral Knee Osteoarthritis (Medial Compartment, Genu Varus) with a Device of the Invention A 68 years old patient presented to the clinic with a major complaint of bi-lateral knee OA.

Anamnesis: Patient complained on bi-lateral knee pain, primarily in the left knee that lasted for 5 years prior to the visit. Patient experienced gradual pain increase and decrease in function (walking, ascending and descending stairs). Pain degree while walking was 6/10 (on a visual analogue scale of 10 cm, higher value means more severe). Patient suffered from moderate stiffness in the morning hours and a severe difficulties in getting out of cars.

Physical examination: Thigh muscles were atrophied. Knees were in varus alignment with limited knee extension on both sides (Lt.: −10°, Rt.: −5°). Palpation was characterized by tenderness on the medial joint line on the left and knee and in the pes anserinus region in the left knee. The right knee was also characterized by tenderness likewise the medial joint line and pes anserinus region were also characterized by tenderness. During walking patient experienced pain in the medial joint line in both knees in the heel-strike phase (VAS 5/10 in the left knee and 3/10 in the right knee). Patient also experienced pain in the pes anserinus region in the mid-stance to toe-off phase.

Imaging and lab: Knee X-ray in standing position: Antero-Posterior view reveals a joint space narrowing on the medial compartment and osteophytes, Kellgren & Lawrence classification 3 in both knees. Gait lab results (see table 1) showed velocity of 93 cm/sec, single limb support of 37.0% in the left leg and 38.1% in the right knee Step length: Left.: 61 cm Right 0.60 cm.

TABLE 1

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1$^{st}$ (initial) | 93 | 61 | 60 | 37.0 | 38.1 |
| 2$^{nd}$ (first follow-up) | 99 | 64 | 63.2 | 37.4 | 38.3 |
| 3$^{rd}$ (second follow-up) | 106 | 65 | 64.2 | 37.7 | 38.5 |
| 4$^{th}$ (third follow-up) | 110 | 65.5 | 65.0 | 38.0 | 38.6 |

Treatment

Bulbous protuberances (BPs with the lowest convexity (A) and soft hardness or resilience were placed under the hind foot and fore-foot.

Balancing: Patient was balanced by visually by reducing eversion and inversion through heel-strike, mid-stance and toe-off.

Pain: In order to reduce pain in the right medial knee joint line in heel-strike posterior right BP was shifted 1-2 mm laterally and fixed. Patient was then asked to walk 20 m with the device and reported reduction of pain from 5/10 to 3/10. Posterior right element was shifted 1-2 mm further laterally. Patient reported that pain disappeared in the right medial joint line while walking with the device.

In order to reduce the pain in the right pes anserinus, the anterior right BP was shifted 1-2 mm medially. At this point the patient reported he had no more pain in the right pes anserinus region while walking with the device.

In order to reduce pain in the left medial knee joint line in heel-strike the left posterior BP was shifted 1-2 mm laterally. Patient than reported a reduction of walking pain from 5/10 to 3/10 when wearing the device. After the left posterior BP was shifted 1-2 mm laterally the patient reported further reduction of pain to 2/10 in the left medial knee joint line while walking with the device. A further lateral shift of the left posterior BP increased the eversion in heel-strike in the left leg so patient was out of balance. Therefore, the left posterior BP was shifted back to the last position (where pain was 2/10 while walking).

In order to reduce the pain in the left pes anserinus, the anterior left BP was shifted 1-2 mm medially. At this point the patient reported a reduction of pain in the left pes anserinus region while walking with the device. After the left anterior BP was shifted additional 1-2 mm medially, pain disappeared in the left pest anserinus region upon walking with the device.

Heel-rise timing: Patient was asked to walk 20 m in order to confirm that he was still balanced and the heel-rise timing is proper. It was noted that the patient had early heel-rise in both right and left leg. At this phase a 2 mm hard spacer was placed between the left posterior BP and the left shoe in order to bring the left foot to a slight plantar-flexion. This time heel rise timing was proper in the left leg. At this phase a 2 mm hard spacer was placed between the right posterior BP and the right device in order to bring the right foot to a slight plantar-flexion. This time heel rise timing was proper in the right leg as well as in the left leg.

Prescription: On week 1 Patient was briefed with safety instructions and was asked to wear the device at home for 45 minutes daily (and walk in accumulative about 5 minutes a day as part of his daily activities at home). Patient was instructed to increase daily wearing time of the device by 5 minutes every week for the initial 6 weeks, reaching 75 minutes wearing time with the device every day (12-15 minutes of accumulative walking). Patient was monitored in the treatment center 6 weeks after his first visit, 3 months after his first visit, and 6 months after his first visit.

Treatment: Patient immediately reported reduction in pain while walking with the device; patient gradually reported a decrease in pain also when walking without the device device. In the follow-up visits gait velocity was increased to 110 cm/sec an increase in step length of 65.5 cm in the left leg and 65.0 cm in the right leg, was observed. Single limb support bi-laterally was increased to 38.0% in the left leg and 38.6% in the right leg, patient had a lower difference between the single limb support of the right and the left leg (a more symmetric gait). After 10 weeks of treatment the patient reported that pain was substantially reduced during walking without the device and he found it much easier to stand for long periods. Patient gradually increased the daily use of the device, until reaching a daily usage of up to 3 hours a day. After 3 months patient was also allowed to walk outdoors with the device. After the initial 6 months patient continued follow-up visits twice-three times a year.

Example 2: Treating a Patello-Femoral Pain Syndrome (Hyper-Laxity and Genu Valgus) with a Device of the Invention A 30 years old female patient presented to the clinic with a diagnosis of patello-femoral pain syndrome.

Anamnesis: Patient complained of suffering from bi-lateral knee pain for the last 5 years. Left knee was more painful than the right knee. During the last 6 months there was an exacerbation in pain level to a level of approx. 5/10 on a visual analogue scale (exacerbation appeared following an intensive day of cleaning the house). She reported that she experiences anterior knee pain during sitting with flexed knees for over 20 minutes (moviegoers' knee). The patient who was an amateur dancer and ceased dancing since pain intensified. Patient reported of being extra flexible since childhood.

Physical examination: Patient had valgus alignment and recurvatum in both knees. On palpation tenderness was noted on the medial side of the patella. Patellar compression test was positive. When examining the patient's gait, patient reported pain is in the medial side of the patella while walking, pain appeared in heel-strike and is higher in the left knee compared to the right knee, 5/10 and 3/10, respectively.

Imaging/Gait: X-ray of the knees showed a slight later-alization of the patellae in the left and right knees. Gait lab results showed a velocity of 110 cm/sec, single limb support of 41.8% in the right leg and 42.4% in the left knee. Step length: Left: 57 cm Right 0.58 cm.

Treatment: identical BPs with B convexity and "hard" hardness or resilience were placed under the hind foot and fore-foot in the left and in the right leg. A 100 g spacer (disc shape) of 3 mm was introduced between the outsole and the posterior BP under the left leg and the right leg and (in order to maintain the anterior BPs at the same height and not create a plantar flexion) a hard spacer and a soft spacer were introduced between the anterior BP and shoe both under the left leg and the right leg.

Balancing: Patient was balanced by visually, reducing eversion and inversion through heel-strike, mid-stance and toe-off.

Pain: In order to reduce pain in the right patella in heel-strike posterior BP was shifted 3 mm anteriorly and 2 mm medially under the right leg. Patient then reported feeling no pain in the right knee while walking with the device. In order to reduce pain in the left patella in heel-strike posterior BP was shifted 3 mm anteriorly and 2 mm medially under the left leg. Patient then reported feeling a 70% decrease in pain at the medial side of the patella in the left knee while walking with the device. At this point posterior BP of the left foot was shifted further 1 mm anteriorly. Patient reported that walking with the current configuration of the device left her only with very mild pain (1-2/10) in the medial side of the left patella.

Heel-rise timing: Patient was asked to walk 20 m in order to confirm that she is still balanced and the heel-rise timing is proper. It was noted that the patient had delayed heel-rise in both right and left foot. At this phase a 2 mm hard spacer was placed between the left anterior BP and the left shoe in order to bring the left foot to a slight dorsi-flexion. Patient was observed walking with the device—heel rise timing was proper in the left foot. At this phase a 2 mm hard spacer was placed between the right anterior BP and the right shoe in order to bring the right foot to a slight dorsi-flexion. Patient was observed walking with the device—heel rise timing was now proper in the right leg.

Prescription: Patient was briefed with safety instructions and was asked on week 1 to wear the device at home for 45 minutes daily (and walk in accumulative about 5 minutes a day as part of his daily activities at home). Patient was instructed to increase daily walking time with the device by 5 minutes every week for the initial 4 weeks, reaching 60 minutes wearing time of the device every day (accumulatively walking or standing 7-10 minutes a day). Patient was monitored in the treatment center 4 weeks after her first visit, 10 weeks after her first visit, and 5 months after her first visit.

Treatment course: Patient immediately reported reduction in pain while walking with the device; patient gradually reported a decrease in pain also when walking without the device to a level of 2/10 after 3 months. She was now able to sit for long periods of time without pain and walked painlessly without the device. In the follow-up visits an increase in step length bi-laterally, a decrease in step length difference, a decrease in single limb support bi-laterally (towards 40%) and a decrease in single limb support difference (see table 2 for gait parameters) were observed. Patient gradually increased the daily use of the device, until reaching a daily usage of 2 hours after 5 months (accumulative walking of 20 minutes a day). After 5 months patient arrived to 2-3 follow-ups every year.

Upon admission pain in the left knee is 6/10 (on a visual analogue scale of 10 cm) in the medial joint line. Patient reports that he suffered great pain upon walking and unable to fully extend his knee.

Physical examination: In inspection the knees are in varus alignment. The left knee is slightly flexed when standing and a mild atrophy of the VMO muscle is apparent. Patient had limited left knee extension of: 10°. In palpation there was tenderness on the medial joint line of the left knee and McMurray's Test for the left medial meniscus was positive. Patient did not extend his left leg fully when walking. Patient reported of pain in the medial joint line in the left knee in the heel-strike phase.

Imaging and lab: Knee X-ray while standing: Antero-Posterior view showed mild changes in the medial compartment bi-laterally. In MRI a radial tear of the posterior horn of the left medial meniscus was observed. Gait lab results (see table 3) showed velocity of 85 cm/sec, single limb support of 35.6% in the left leg and 39.5% in the right leg Step length: Left.: 60 cm Right 0.58 cm.

TABLE 2

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| $1^{st}$ (initial) | 110 | 58 | 57 | 42.4 | 41.8 |
| $2^{nd}$ (first follow-up) | 117 | 61 | 60.2 | 42.0 | 41.5 |
| $3^{rd}$ (second follow-up) | 120 | 63 | 62.3 | 41.6 | 41.1 |
| $4^{th}$ (third follow-up) | 125 | 64 | 63.5 | 41.1 | 40.7 |

Example 3: Treating a Degenerative Medial Meniscus Tear (Radial Tear in the Posterior Horn of the Medial Meniscus) with a Device of the Invention 57 years old patient presented to the clinic with a major complaint of left medial meniscus tear.

TABLE 3

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| $1^{st}$ (initial) | 85 | 60 | 58 | 35.6 | 39.5 |
| $2^{nd}$ (first follow-up) | 95 | 63 | 61.3 | 36.9 | 39.3 |
| $3^{rd}$ (second follow-up) | 107 | 66 | 64.5 | 37.5 | 39.3 |
| $4^{th}$ (third follow-up) | 120 | 68 | 67 | 38.5 | 39.5 |

Anamnesis: Patient suffered from occasional knee pain for the last 6 years with symptoms alternating between left and right knees. 4 weeks prior to arrival to the clinic he had an event of acute pain in his left knee while having is evening walk. He ruled out any knee trauma.

Therapy: identical BP's with the B convexity were fixed under the hind-foot and fore-foot of the patient's right foot. BPs had "soft" hardness. Under the left foot two BPs with C convexity (which is higher than B) were placed under the hind-foot and fore-foot. BP's under the left foot had higher convexity in order to introduce higher perturbation/instability under the left foot, thus, allegedly, promoting more coordinated recruitment of muscles and reducing the muscle guarding of the left knee. The higher convexity under the left foot also provided additional height compared to the right foot, thus promoting "off loading" (a shift of weight of the body from the affected, left leg to the right leg).

Balancing: Patient was balanced by visually reducing eversion and inversion through heel-strike, mid-stance and toe-off.

Pain: In order to reduce pain in the left medial knee joint line in heel-strike posterior left BP was shifted 1-2 mm laterally. Patient reported pain in the left medial joint line was reduced while walking with the device from 6/10 to 4/10. At this point left posterior BP was shifted 1-2 mm further laterally. Patient reported that the pain was further reduced to 2/10. Left posterior BP was shifted 1-2 mm further laterally. After the last lateral shift it was noted that upon heel strike the patient went into increased eversion and therefore, the left posterior BP was fixed back in the previous position (Where pain was 2/10).

Heel-rise timing: Patient was asked to walk 20 m in order to confirm that he is still balanced and the heel-rise timing is proper. An early heel-rise in the left leg was observed. A soft spacer of 2 mm was introduced between the posterior left BP and the device. Once the patient walked with the device, heel rise timing was corrected for the left leg. In this case, the spacer was a soft spacer in order to reduce the impact in heel strike.

Prescription: Patient was briefed with safety instructions and was asked to wear the device at home for 45 minutes a day on week 1 (and walk in accumulative about 5 minutes a day as part of his daily activities at home). Patient was instructed to increase daily wearing time of the device by 5 minutes every week for the initial 3 weeks, reaching 60 minutes wearing time with the device every day (8-10 minutes of accumulative walking or standing). Patient was monitored in the treatment center 3 weeks after his first visit, 6 weeks after his first visit, and 3 months after his first visit.

Treatment: Patient immediately reported reduction in pain while walking with the device; patient gradually reported a decrease in pain also when walking without the device. After 3 months of treatment pain in the left knee was decreased to 2/10. Gait (see table 3) velocity was increased, an increase in step length of the left and right leg was observed and single limb support was increased in the left leg and in the right leg. Patient had a lower difference between the single limb support of the right and the left leg (a more symmetric gait). The patient reported an increasing alleviation of pain whilst walking with street shoes or barefooted. Clinical visual gait assessment showed full extension of the left knee during the stance phase Once pain was reduced, full extension reached and the symmetry in single limb support improved the different calibrations on the right and left systems was evened out. The patient had "C" BP's under the hind-foot and the fore-foot of both legs. The additional soft spacer was removed from under the posterior left BP Patient gradually increased the daily use of the device, until reaching a daily usage of up to 2 hours a day. After 3 months patient was also allowed to walk outdoors with the device. After the first 6 months, patient arrived to the center 2-3 times a year for follow-up visits. The additional spacer that was introduced between the posterior left BP and the shoe was removed after the difference in single limb support was reduced below 2%.

Example 3: Left Anterior Cruciate Ligament Tear (No Pain) with a Device of the Invention A 27 years old patient presented to the clinic with a major complaint of left Anterior Cruciate Ligament (ACL) tear. Anamnesis: 2 months prior coming to the clinic the patient twisted his left knee in a soccer game. Following this event the knee got swollen and painful. Patient was treated in a physiotherapy clinic since the injury and suffered no pain but had experienced, twice a week, events of "giving-way" in the left knee. He was also unable to enjoy in activities such as soccer, running or jumping.

Physical examination: On observation the knees were in a varus alignment. Anterior drawer test was positive in the left knee. McMurry and valgus stress tests were negative. Imaging and lab: MRI revealed that a left ACL tear is present. Gait lab results (see table 4) showed velocity of 110 cm/sec, single limb support of 38.2% in the left leg and 40.5% in the right leg Step length: Left.: 63 cm Right: 62 cm.

TABLE 4

Patient's gait parameters

| Visit | Velocity (cm/sec) | Left step length (cm) | Right Step length (cm) | Left Single Limb Support (in % of step cycle) | Right Single Limb Support (in % of step cycle) |
| --- | --- | --- | --- | --- | --- |
| 1$^{st}$ (initial) | 110 | 63 | 62 | 38.2 | 40.5 |
| 2$^{nd}$ (first follow-up) | 123 | 66 | 65.2 | 39.0 | 40.3 |
| 3$^{rd}$ (second follow-up) | 135 | 70 | 69.5 | 39.5 | 40.1 |
| 4$^{th}$ (third follow-up) | 140 | 72 | 71.6 | 39.9 | 40 |

Therapy: identical BPs with B convexity and "hard" hardness were fixed under the hind-foot and fore-foot of the patient's right foot and the patient's left foot. A 100 g weighted spacer (disc) of 2 mm was introduced between the footwear and the posterior BP under the left foot and the right foot and (in order to maintain the anterior BPs at the same height and to avoid a plantar flexion) a hard and a soft spacers was introduced between the anterior BP and outsole both under the left foot and the right foot. The weighted spacer was introduced in order to induce increased activity in the muscles of the left leg and right leg. BPs convexity was planned to be increased as the treatment progressed.

Balancing: Patient was balanced by visually reducing eversion and inversion through heel-strike, mid-stance and toe-off.

Pain: Patient had no pain and was calibrated according to the balancing criteria.

Heel-rise timing: Patient was asked to walk 20 m in order to confirm that he is still balanced and the heel-rise timing is proper. Heel-rise was proper.

Prescription: Patient was now briefed with safety instructions and was asked on week 1 to wear the device at home for 1 hour a day (and walk in accumulative about 10-15 minutes a day as part of his daily activities at home). Patient was instructed to increase daily wearing time of the device by 10-15 minutes every week for the initial 3 weeks, reaching 90 minutes wearing time with the device every day (about minutes of accumulative walking a day). Patient was monitored in the treatment center 3 weeks after his first visit, 6 weeks after his first visit, and 3 months after his first visit.

Imaging and Gait lab: X-rays in the supine position revealed right hip joint space narrowing with subchondral bone sclerosis and subchondral bone cysts. The left hip showed joint space narrowing to a lesser degree. Gait lab data provided: gait velocity of 91 cm/sec, right step length: 55 cm, left step length 52.3 cm, right single limb support 37.3% and left single limb support 39.1%. In/out toeing angle of the foot was −3.1 degrees on the right (indicating 3.1 degrees of in-toeing) and +5 degrees on the left (indicating 5 degrees of out-toeing) (see table 5 for gait lab data).

TABLE NO. 5

| | Patient Gait Parameters | | | | | | |
|---|---|---|---|---|---|---|---|
| Visit | Velocity (cm/sec) | Left step length (cm) | Right Step length (cm) | Left Single Limb Support (in % of step cycle) | Right Single Limb Support (in % of step cycle) | Left In/Out Toeing (+out − in) | Left In/Out Toeing (+out − in) |
| 1$^{st}$ (initial) | 91.0 | 55.0 | 52.3 | 39.1 | 37.1 | −3.1 | +5 |
| 2$^{nd}$ (first follow-up) | 95 | 56.1 | 54.5 | 39.0 | 38.0 | −2.7 | +6.1 |
| 3$^{rd}$ (second follow-up) | 100 | 56.5 | 54.9 | 39.3 | 38.5 | −1.3 | +6.5 |
| 4$^{th}$ (third follow-up) | 108 | 56.4 | 55.3 | 39.4 | 38.6 | −1.2 | +6.4 |

Treatment course: Patient reported a significant reduction in "giving-ways" already after 3 weeks of treatment, in gait lab velocity was higher; step length and single limb support were increased in the left and in the right knee. In the first follow-up meeting the BPs convexity was increased to "C" under the hind-foot and the fore-foot both in the left and in the right leg. After 6 weeks of treatment, the patient was also given designated exercise to incorporate with the device. After 3 months of treatment, patient returned to play soccer as an amateur. The convexity of all 4 BPs was gradually increased. The daily usage of the device was increased until reaching up to 3 hours daily wearing time both indoors and outdoors.

Example 4: Hip Osteoarthritis

A 72 years old female patient presented to the clinic with pain, difficulty in walking, difficulty ascending stairs and difficulty in prolonged standing.

The patient reported having pain in the area of the right greater trochanter and the inguinal area. The pain was felt during walking, getting up from a seated position and while ascending stairs. The patient had the pain for the past year and reported it was gradually worsening. She also described stiffness around the right hip area after getting up in the morning lasting for 15 minutes.

Physical Examination: On observation the patients' knees are in a mild valgus alignment and she stands with an anterior pelvic tilt (flexion deformity of the right hip). Internal rotation of the right hip in neutral position was full but painful at the end of range. Right hip internal rotation in 90 degrees of flexion was 15 degrees and painful (30 degrees in the left hip). FADIR test was positive on the right and negative on the left. Right hip extension showed limited range of motion in comparison to the left (10 degrees and 25 degrees respectively). Clinical gait assessment revealed increased pelvic posterior rotation on the right during late stance. The patient reported she feels the inguinal pain during both heel strike and late stance. She rated the pain as 4/10 on VAS.

Treatment course: BP's with B (medium) convexity and "soft" resilience/hardness were connected and fixed under the hind-foot and fore-foot of the left and right footwear. A 100 g spacer (disc shaped) of 3 mm height was attached and fixed between the outsole and the posterior protuberance under both legs. In order to maintain the anterior protuberance at the same height so as not to create a plantar flexed position a hard spacer and a soft spacer were introduced and fixed between the anterior protuberance and footwear both under legs.

Balancing: The patient's device was calibrated and fine tuned during repeated clinical gait assessments with the device (footwear). During this process care is taken to reduce the eversion and inversion during heel strike, loading response, mid-stance and toe-off.

Pain: In order to reduce the pain in the right inguinal area during heel strike the posterior Rt. BP was calibrated 3 mm posterior and 2 mm medially. The patient reported that pain was reduced to a 2/10 (from a level of 4/10). To reduce the pain further the posterior right BP was calibrated and fixed in a new position (1 mm posteriorly and 1 mm medially). The patient reported that pain during heel strike was reduced to a mild discomfort. However, the foot seemed to be inverting during heel strike phase so the posterior Rt. BP was calibrated and fixed 1 mm lateral to its previous position. As a result the pain was decreased to a level of 1/10 while walking with the system. The left system was balanced and further calibrated to minimize eversion and inversion through all phases of the stance.

Heel-Rise Timing: The patient was asked to walk 20 meters in order to see if the heel-rise was timed in the gait cycle. It was noted that the patient had a late heel-rise in both the right and the left leg. In order to correct this, another 2 mm hard spacer was fixed between the right anterior BP and the right boot, thus bringing the right ankle into a more plantar flexed position. The patients gait was reassessed and the heel rise observed on the right was normalized. The patient reported at this point that she felt a significant decrease in the pain during late stance (0.5 on VAS). This is allegedly because the dorsi-flexion created reduced the need for hip extension at this phase of gait. Thus, the patient was better supported by the footwear. In order to correct the timing of the left heel-rise another 2 mm hard spacer was fixed between the left anterior BP and the left boot, thus bringing the left ankle into a more plantar flexed position. The patient's gait was reassessed: left heel rise was normalized.

Treatment Plan: The patient was briefed about the safety instructions of the device and instructed to start the treatment with a total wearing time of 30 minutes a day for the first week of the treatment (accumulative weight bearing time was defined as 15% of total wearing time, i.e. 5 minutes). She was asked to increase the total wearing time of the device by 10 minutes a week for the first 6 weeks of the treatment, maintaining the relative 10% of accumulative weight bearing time. The patient was seen for follow up consultations 6 weeks after the initial consultation, 3 months after the initial consultation and 5 months after the initial consultation.

Treatment Progression: As described above during the initial consultation, the patient had an immediate reduction in pain while walking with the calibrated device. On the first follow up consultation the patient reported that she found house work much easier than previously and less painful. Follow up Gait lab results indicated an increase in velocity, step length and single support in both legs as well as an improvement in the symmetry of gait. The patient was asked to continue to add to the total wearing time at a rate of 15 minutes per week while increasing the accumulative weight bearing time to 15% of the total wearing time.

On the second follow up the patient reported that morning stiffness was substantially reduced and she found that walking outside without the device is easier. She reported she currently feels the pain around the greater trochanter when she walks for over 45 minutes (VAS 1-2/10). The pain in the inguinal area was very infrequent. By then, the patient was wearing the device for 4 hours a day and functioning indoors freely (Gait lab data provided in table no. 5). The posterior BP's on both devices were changed to C convexity (more convex) in order to provide a greater challenge for her neuromuscular system. Since C convexity protuberances are higher than the B convexity protuberances (which remained unchanged in the anterior protuberance on both the device on the left foot and the device on the right foot) a hard spacer was introduced between the outsole and the base of the anterior protuberance on both the right and the left boots. This was done without changing the location of the anterior protuberances. Following this calibration, the patient's gait was reassessed including balanced calibration (as explained above). The patient reported she had no pain or discomfort with the new calibration. She was instructed to maintain the overall treatment time.

After the initial 5 months the patient was seen twice a year for follow up consultations and monitoring. Her walking abilities and pain improved dramatically.

Example 5: Left Total Knee Replacement and Right Knee OA

A 71 years old male presented to the treatment center 3 months after undergoing a left total knee replacement.

Case History: The patient suffered from OA of the left knee for 5 years prior to undergoing an elective TKR. He suffered right knee medial and anterior pain for the last 2 years. The patient reported that he had physiotherapy for 3 months post surgery but he feels weak in the injured leg. He also reported of an increase in medial pain in the right knee since the surgery which he rated as 6/10 at its worst.

Physical Examination: On observation the patient bears more weight on the right leg, quadriceps and triceps surae on the left are atrophied compared to the right. Assessment of range of motion in the supine position revealed full extension of the right and left knees. Flexion on the right was 110 degrees and 120 on the left with left medial knee pain produced at the end of range. Palpation did not produce any pain in the left knee and produced medial joint line tenderness on the right knee. During clinical gait assessment the left knee was observed to have inadequate flexion during swing phase which resulted in circumduction of the hip as compensation. During stance phase the left knee did not fully extend and was kept at about 10 degrees flexion. The patient reported medial knee pain in the left knee was felt mainly during heel strike and loading phases. He rated that pain as 4/10 on VAS.

Imaging and Gait lab: X-rays in the supine position (regrettably X-rays in standing were unavailable at the initial consultation) showed the TKR prosthesis was well positioned and did not show any signs of infection or loosening. The left knee X-rays revealed mild-moderate medial joint space narrowing. Kellgern-Lawrence rating was impossible since X-rays were in supine. Gait lab data revealed: a gait velocity of 68 cm/sec., left single limb support: 32.3%, right single limb support 37.2%, left step length 51.1 cm. and right step length was 46.5 cm. (see table 6 for detailed gait lab data).

TABLE 6

Patient Gait Parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1$^{st}$ (initial) | 68.0 | 51.1 | 46.5 | 32.3 | 37.2 |
| 1$^{st}$ (initial) With the Device | 80.0 | 55.2 | 49.5 | 35.1 | 36.2 |
| 1$^{st}$ (initial) Barefoot retest | 74.2 | 55.0 | 48.1 | 33.8 | 36.9 |
| 2$^{nd}$ (first follow-up) | 79.3 | 58.1 | 56.3 | 35.8 | 37.9 |
| 2$^{nd}$ (first follow-up) With the Device | 88.6 | 59.4 | 58.1 | 36.7 | 38.3 |
| 2$^{nd}$ (first follow-up) Barefoot retest | 85.6 | 58.8 | 58.0 | 36.4 | 37.9 |
| 3$^{rd}$ (second follow-up) | 103.2 | 60.9 | 59.2 | 38.7 | 38.0 |
| 3$^{rd}$ (second follow-up) With the Device | 115.3 | 62.3 | 60.9 | 38.9 | 38.3 |
| 3$^{rd}$ (second follow-up) Barefoot retest | 110.4 | 61.7 | 60.7 | 38.1 | 38.9 |
| 4$^{th}$ (third follow-up) | 115.9 | 62.5 | 61.9 | 38.2 | 38.1 |
| 4$^{th}$ (third follow-up) With the Device | 117.2 | 63.0 | 62.4 | 37.9 | 38.0 |

Therapy: BP's with B convexity and "soft" resilience were attached and fixed under the hind-foot and the fore-foot of the left device. BP's with C convexity and "soft" resilience were attached and fixed under the hind-foot and the fore-foot of the right foot. Since C convexity BP's are higher than B convexity Protuberances, and since gait lab data showed the patient has reduced single limb support on the left leg, 3 hard spacers were inserted and fixed under the anterior and posterior BP's of the left foot. This calibration, called "off-loading", induces easier swing of the contralateral leg by increasing the height of the BP's in the affected leg. In this case the left leg is 3 mm. higher than the right leg.

In order to increase proprioceptive input, a 100 g disc was inserted between the shoe and the posterior B.P. of the left and right systems. This brought both ankles to a slightly plantar flexed position. This was not corrected since the left knee failed to reach full extension during stance the plantar flexion is supports it.

Balancing: The patients system was calibrated and fine tuned during repeated clinical gait assessments with the device. During this process care is taken to reduce the eversion and inversion during heel strike, loading response, mid-stance and toe-off.

Pain: In order to reduce the pain in the right medial knee the posterior BP of the right system was calibrated 2 mm. laterally and fixed in the new position. The patient then reported that his pain has reduced to 3/10 while walking with the device. The posterior protuberance of the right system was therefore calibrated another 2 mm. laterally and fixed in the new position. When the patient walked with the device again the pain was reduced to 1/10. The posterior protuberance of the right device was calibrated and fixed a further 1 mm. laterally but clinical gait assessment showed that the right foot was now excessively pronated and the patient did not report any further decrease in pain. The posterior BP of the right system was therefore recalibrated to its previous position and fixed there. Clinical gait assessment showed that the eversion of the right foot was now at an acceptable amount and the patient rated the medial knee pain as 1/10.

In order to improve the extension of the left knee during stance the posterior BP of the left footwear was calibrated and fixed 5 mm. anterior to its neutral position. The knee seemed to be more extended during stance phase and the gait velocity was increased. The patient reported that walking with the footwear is much more comfortable than walking with regular sneakers.

Heel-Rise Timing: The patient was asked to walk 20 m in order to confirm that he was still balanced and the heel-rise is well timed in the gait cycle. The clinical gait assessment showed an early heel rise on the left leg. In order to correct this, a hard spacer was introduced and fixed under the posterior BP in the left footwear. Repeated gait assessment showed that the left heel-rise had been normalized.

Gait lab Retest: Once the balancing process was completed the patient performed another gait lab test with the device. The results of this test were significantly better than the baseline results. Gait velocity increased to 80 cm/sec., left single limb support: 35.1%, right single limb support 36.2%, left step length 55.2 cm. and right step length was 49.5 cm. (see table 6 for detailed gaitlab data). The data from this test showed gait velocity was 74.2 cm/sec., left single limb support: 33.8%, right single limb support 36.9%, left step length 55.0 cm. and right step length was 48.1 cm. (see table 6 for detailed gaitlab data). These results show that the patients gait is much improved with the device and that some of the improved motor control (for example the improved left knee extension during stance) is retained for at least a short period of time.

Treatment Plan: The patient was briefed with safety instructions and instructed to start the treatment by wearing the device for an hour and a half daily on the first week of the treatment. Accumulated weight bearing time was set at 10% of the total time of wearing the footwear. Thus out of the hour and a half he was supposed to be in weight bearing for an accumulative period of 9-10 minutes. The patient was asked to increase the total wearing time of the footwear by 15 minutes on the second week, maintaining the relative 10% of accumulated weight bearing time. The patient was seen for follow up consultations 2 weeks after the initial consultation, 6 weeks after the initial consultation, 3 months and again 6 months after the initial consultation.

Treatment Progression: As mentioned above the patient felt an immediate pain relief in the right knee and had better knee extension on the left when walking with the footwear during the initial consultation. During the second follow up consultation the patient reported that he enjoyed walking with the footwear and found it easier and less painful to walk and function with it. The pain in the right knee was not constant now though its peak level did not decrease (VAS 6/10). Gait lab test revealed an increase in left single limb support (from 32.3% to 33.9%) and an increase in right step length (from 46.5 cm. to 47.3 cm, for gait lab details see table no. 6). Due to the improvement and due to the fact that differences between right and left single limb support and step length were still significant the calibration of the right and the left boots was left unchanged. The patient was asked to increase the total wearing of the footwear by 15 minutes per week. In addition he was instructed to walk continuously with the device indoors, starting from 2 minutes of continuous walking and increasing by 2 minutes every week.

On the second follow up the patient reported that he reached 2.5 hours of total wear time, out of which he had an accumulative weight bearing time of 15-20 minutes. In addition, he reported that he had much less pain in the right knee while performing daily activities without the footwear (VAS 3/10). Gait lab data revealed further increases in gait velocity (79.3 cm/sec.), left single limb support (35.8%) and right and left step length (56.3 cm. and 58.1 cm. respectively). These results represent a marked improvement in gait symmetry and mirror the patients' report of improvement in pain level and functional level. The calibration was therefore changed to C convexity on the anterior and posterior BP's of the left device. The hard spacer on the posterior protuberance of the left device was removed since the knee extension on barefoot gait was now full. The calibration in the right device remained unchanged. The patients gait was reassessed with the device and there were no gait deviations observed. The patient reported he felt comfortable walking with the new calibration and did not experience any symptoms. A gait lab test with the footwear was performed and showed encouraging results, as did a barefoot gait lab retest (see detailed results in table 6). The patient was asked not to increase wearing time as to allow for a customization process to take place. He was told to gradually increase total wearing time to 4 hours and increase accumulative weight bearing time to 15% of the total wearing time. In addition he was instructed to increase his indoor walking gradually to 15 minutes.

The patient continued his gait improvement and pain relief. On the third follow up consultation he was allowed to perform outdoor walking with the Device. Gait lab results are shown in table 6. The patient was seen again for a follow up consultation 6 months after the initial consultations in which he reported he had no pain or weakness in the left leg and had only mild (1-2/10) occasional pain in the medial aspect of the right knee. After this the patient was asked to come in for follow up consultations twice a year.

Example 6: Post Left Total Hip Replacement

A 75 years old male is presented to the treatment center 3 weeks following an elective right total hip replacement.

Case History: The patient had left hip pain for four years prior to surgery, with a significant increase in pain and functional limitations during the year prior to surgery. During the surgery a cemented total hip prosthesis was inserted. He was told to bear full weight on the operated leg but was unable to do so due to pain and fear that it will not support him. At the time he was first seen he is ambulating with a walker and confined to indoor walking only. Pain was felt around the surgical wound and deep in the groin area (VAS 5/10).

Physical Examination: On observation in standing the patient bears significantly more weight on the right leg and stands in forward flexion of the trunk. Ranges of motion measured in supine were: hip flexion—left: 80 degrees, right: 105 degrees. Internal rotation in neutral position—left: 15 degrees, right: 25 degrees. During clinical gait assessment the patient had great difficulty walking without the walker so the assessment was very minimal. The patient rated the pain as 5/10 on VAS and described the left leg as being very weak Imaging and Gait lab: X-rays showed the prosthesis was in good position without any signs of loosening or infection. The right hip showed mild joint space narrowing. Gait lab results showed gait velocity was 37 cm/sec., left step length—21 cm, right step length—25 cm, left single limb support—19.0%, right single limb support—42.1%.

Therapy: BP's with A level of convexity (low level) were attached and fixed under the hind-foot and fore-foot of the left device. BP's with C level (high level) of convexity were attached and fixed under the hind-foot and fore-foot of the right device. A 100 g spacer (disc) was inserted and fixed between the outsole and the posterior BP's of the left and the right footwear in order to increase the proprioceptive input during swing and improve pelvic muscular control during stance. In order to support the patient in the forward flexed position (and correct the plantar flexed position created by the insertion of the disc in the posterior BP's) 2 hard spacers and a soft spacer were inserted and fixed between the shoe and the anterior BP's on the left and the right devices. Since C convexity provides elevated height than convexity A, balancing was required. Because of the vast difference in single limb support between the left and right legs there was a need to "off-load" the left leg (for details about the rationale of off-loading see previous examples). For that purpose 2 hard spacers were inserted between the outsole and the anterior protuberance of the left boot. 2 additional hard spacers were inserted between the outsole and the base of the anterior BP of the left device.

Balancing: The patient's footwear was calibrated and fine tuned during repeated clinical gait assessments with the device. During this process care is taken to reduce the eversion and inversion during heel strike, loading response, mid-stance and toe-off.

Pain: In order to decrease the pain in the left hip during weight bearing, the posterior protuberance of the left footwear was calibrated and fixed 6 mm posteriorly and 4 mm medially to its previous position. The patient reported that pain decreased to a level of 4/10 on VAS and he found that bearing weight on the leg is now, easier. The posterior left BP was calibrated and fixed a further 2 mm posteriorly and 2 mm medially and the patient reported another decrease in pain level (3/10) and comfort in weight bearing. During clinical gait assessment it was clear that the gait velocity has increased and weight bearing on the left leg was performed with more movement into hip extension. This process continued until the posterior left BP was fixed 15 mm posteriorly and 8 mm medially to its original position. The patient had a marked improvement in pain (VAS 2/10) and symmetry of gait. The same process was repeated with the right device (i.e. the position of the posterior device was recalibrated and fixed to a more posterior and medial position and the patients' gait was reassessed). At the end of the calibration of the right boot, the posterior device was 9 mm posteriorly and 6 mm medially to its original position.

Heel-Rise Timing: The patient was asked to walk 20 m in order to confirm heel-rise is well timed in the gait cycle. An early heel-rise in the right foot was evident. In order to correct this, the soft spacer was removed from between the anterior BP and the shoe of the right footwear. A clinical gait assessment was performed and it was noted that the heel-rise in the right leg had been normalized.

Gait lab Retest: Once the balancing process was completed the patient performed another gait lab test with the device. The results of this test were significantly better than the baseline results. Gait velocity increased to 55.0 cm/sec., left single limb support: 27.3%, right single limb support 39.1%, left step length 37.2 cm. and right step length was 39.3 cm. (see table 7 for detailed gait lab data). The data from this test showed gait velocity was 49.1 cm/sec., left single limb support: 25.6%, right single limb support: 41.6%, left step length 32.7 cm and right step length was 39.3 cm. (See table 7 for detailed gait lab data). These results show that the patients gait is much improved with the device and that some of the improved motor control (for example the bearing more weight on the left leg thus increasing right step length) is retained for at least a short period of time.

TABLE 7

Patient's Gait lab Parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| $1^{st}$ (initial) | 37.0 | 21.0 | 25.0 | 19.0 | 42.1 |
| $1^{st}$ (initial) With the Device | 55.0 | 37.0 | 40.5 | 27.3 | 39.1 |
| $1^{st}$ (initial) Barefoot retest | 49.0 | 32.7 | 39.3 | 25.6 | 41.6 |
| $2^{nd}$ (first follow-up) | 73.1 | 42.0 | 47.0 | 33.3 | 39.4 |
| $2^{nd}$ (first follow-up) With the Device | 92.8 | 52.3 | 56.6 | 35.1 | 39.0 |
| $2^{nd}$ (first follow-up) Barefoot retest | 80.3 | 46.9 | 49.3 | 34.8 | 39.6 |

TABLE 7-continued

Patient's Gait lab Parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 3$^{rd}$ (second follow-up) | 116.0 | 64.1 | 62.7 | 37.9 | 40.4 |
| 3$^{rd}$ (second follow-up) With the Device | 117 | 65.3 | 64.8 | 37.1 | 39.1 |
| 3$^{rd}$ (second follow-up) Barefoot retest | 115.6 | 64.8 | 64.6 | 37.6 | 39.3 |

Treatment Plan: The patient was briefed about the safety instructions and instructed to start the treatment by wearing the device for a total time of one hour for every day of the first week, out of which a total of 5% to 10% should be spent in weight bearing activities. Thus accumulated weight bearing time should be 3-6 minutes. The patient was seen for follow up consultations 10 days after the initial consultation, 3 weeks after the initial consultation, 5 weeks after the initial consultation and 3 months after the initial consultation.

Treatment Progression: At the end of the initial calibration process the patient immediately felt less pain and his ambulation was much easier with the footwear. In the first follow up he reported that pain was decreased while walking with the footwear (to 1/10 on VAS). He also reported that when he was walking with the footwear he did not need the support of the walker. Gait without the footwear was also significantly better with pain level rated at a maximum of 3/10. Gait lab results showed a large improvement in barefoot gait. Gait velocity was 73.0 cm/sec., left single limb support: 33.3%, right single limb support 39.4%, left step length 42.0 cm. and right step length was 47.0 cm. (see table 7 for details of barefoot gait lab retest). Due to the improvement and due to the fact that differences between right and left single limb support and step length were still significant the patient still needed "off-loading" and asymmetrical level of perturbation. The anterior and posterior BP's of the left footwear were therefore changed to a B level of convexity. Since B level convexity is higher than the A level convexity, one hard spacer was removed from the posterior BP. This was done without changing the position of the BP. A hard spacer was removed from the anterior protuberance as well, without changing its position. Clinical gait assessment revealed the patient had an early-heel rise in the left leg. In order to correct this one soft spacer was removed from the anterior left BP and the patients' heel-rise timing became normalized. The patient was asked not to increase the total wearing time for 3-4 days to allow his neuromuscular control to get accustomed to the new calibration. After the first 4 days the patient was asked to increase the total wearing time of the footwear by 15 minutes a week and maintain 10% of accumulative weight bearing time.

On the second follow up the patient reported that he no longer needed any type of walking aid. His pain level decreased to 1/10 and he reported he had the device on for 2 and half hours every day. During that time he ambulates freely around the house. Gait lab data showed velocity was now 116 cm/sec, left single limb support: 37.9%, right single limb support 40.4%, left step length 64.1 cm. and right step length was 62.7 cm. (see table 7 for details of barefoot gaitlab retest). The anterior and posterior BP's of the left device were therefore changed to a C level convexity. Since C level convexity is higher than the B level of convexity which the left the BP's had in the last calibration one hard spacer was removed from the posterior protuberance. This was done without changing the position of the BP. A hard spacer was removed from the anterior BP as well, without changing its position. Clinical gait assessment showed no gait deviations and the patient reported he had no pain or discomfort. Gait lab data with the device and a barefoot retest are provided in table. 7. The patient was requested to increase the total wearing time of the footwear by 20 minutes a week. He was instructed that within this time frame he should perform one period of continuous indoor walking starting with 10 minutes and increasing by 2 minutes per week. In the follow up consultation conducted 3 months after the initiation of the treatment the patient reported he was pain free and has worked the overall wearing time of the footwear to 5 hours a day. During that time he performed a 25 minute period of continuous indoor walking (see table 7). There were no changes in the calibration made in this follow up consultation. The patient was instructed to continue with the same treatment plan and cone for another follow up consultation in 5 months.

Example 7: Right Bimalleolar Ankle Fracture (Open Reduction and Internal Fixation)

A 37 years old male is presented to the treatment center 10 weeks after a bimalleolar ankle fracture treated by an open reduction and internal fixation.

Case History: The patient has broken his right ankle during a basketball game 10 weeks ago in an inversion mechanism. He was operated that night and was recommended to maintain the leg in non-weight bearing for two weeks. Following the removal of the staples, partial weight bearing was recommended. The patient was instructed by the treating surgeon to increase weight bearing as tolerated and was referred to physiotherapy. He needed a walking stick for outdoors walking. Walking for over 5 minutes was difficult and painful (4/10 on a VAS). The pain was increasing when climbing up or down stairs (5/10 and 6/10 respectively).

Physical Examination: On observation there was a moderate edema around the right foot and ankle. The patient was bearing more weight on the left leg. Ranges of motion measured by a hand held goniometer revealed right dorsiflexion—5 degrees, left dorsiflexion—15 degrees, right plantar-flexion—45 degrees, left plantar-flexion—75 degrees. Palpation of the ankle produced mild tenderness in the anterior joint line and around the lateral malleolus. During clinical gait assessment it was evident that the patient had insufficient dorsiflexion in the right ankle. This led to a shorter stance on the right and reduced the swing phase of the left leg. The patient reported anterior and lateral right ankle pain during mid and late phases of stance. He rated the pain as 5/10 on a VAS.

Imaging and Gait lab: X-rays of the right ankle showed the fracture to be well positioned and fully calloused. There were no apparent signs of ankle or subtalar joint damage. Gait lab data showed gait velocity of 65.1 cm/sec., left step length—43.8 cm., right step length—50.2 cm, left single limb support—43.2%, right single limb support—31.7%.

Therapy-Balancing: The patient's footwear was calibrated and fine tuned during repeated clinical gait assessments with the device. During this process care is taken to reduce the eversion and inversion during heel strike, loading response, mid-stance and toe-off.

Pain: BP's with a B level convexity and "soft" hardness were attached and fixed under the hind-foot and fore-foot of the right boot. In order to reduce the pain during midstance of the right leg (believed to be caused by the limited dorsiflexion) two soft spacers were inserted and fixed between the posterior right BP and the outsole. This brought the right ankle to a slightly plantar-flexed position. In addition, this also created a certain a degree of "off-loading" of the right leg (see previous examples for details of "off-loading"). BP's with C level convexity and hard resilience were attached and fixed to the hind-foot and fore-foot of the left footwear. Since BP's with C level convexity are higher than BP's with B level convexity, the "off loading" of the right leg was now lost. Therefore, two hard spacers were inserted and fixed between the shoe and the right posterior protuberance, additional two hard spacers were inserted and fixed for the right anterior BP. The patients' gait was clinically assessed and showed increased velocity, longer stance period of the right leg and improved step length symmetry. The patient reported that the right ankle pain was now at a level of 2/10 pain. In order to decrease the right ankle pain further the posterior right BP was calibrated and fixed 3 mm anteriorly to its original position. The patient reported that his right ankle pain level was now 1/10. A further anterior calibration of 2 mm of the right posterior BP did not produce any further improvement in either gait quality or pain level. Therefore, the right posterior BP was calibrated and fixed 2 mm back to its previous position.

Heel-Rise Timing: The patient was asked to walk 20 m in order to confirm that he was still balanced and the heel-rise is well timed within the gait cycle. There were no apparent gait deviations regarding heel-rise timing in the left leg or the right leg.

Treatment Plan: The patient was briefed regarding the safety instructions. He was told to wear the device for a total of 45 minutes a day on every day of the first week. Out of that total time he was asked to perform weight bearing activities for an accumulative amount of 9-10 minutes (20% of the total wearing time). The patient was instructed to increase the total wearing time of the footwear by 10 minutes each week of the treatment, while maintaining 20% of accumulative weight bearing time. The patient was seen for follow up consultations in the Treatment center 2 weeks after the initial consultation, 5 weeks after the initial consultation, 3 months after the initial consultation and half a year after the initial consultation.

Treatment Progression: As afore mentioned, the patient had significantly reduced pain and found walking much easier with the footwear during the initial calibration process. On the first follow up consultation the patient reported that he found walking indoors without the footwear easier and less painful than before (pain level for indoor walking 2/10) though he still needed to use the walking cane for longer, outdoor walks. He increased the total wearing time of the footwear to an hour and 15 minutes. Gait lab data showed gait velocity increase to 78.0 cm/sec, right step length and left step length have increased and the symmetry in step length was better (left—48.9 cm. right—52.3 cm.). The single limb support values also improved and had better symmetry (left—41.0% right—33.2%). Due to the positive effects on pain level and gait parameters the calibration was left unchanged. The patient was asked to increase the total wearing time by 15 minutes each week while maintaining the relative 10% of accumulative weight bearing time.

On the second follow up consultation the patient reported he found walking outdoors much less painful (pain level decreased to 1-2/10) and ceased to use the walking cane. He was wearing the device for 2 hours a day and found walking with it, painless. Gait lab parameters were: velocity—105.5 cm/sec. left step length 54.3 cm, right step length—57.1 cm left single limb support—39.5%, right single limb support—37.8%. Due to the pain decrease and the vast improvement on gait lab parameters the "offloading" and the asymmetry in perturbation was thought to be unnecessary. The anterior and posterior BP's of the right device were changed from B level convexity to C level convexity. The soft spacers placed between the outsole and the base of the posterior right BP were removed and then the BP was fixed to the same position. The patients gait was reassessed and the patient reported that he felt mild pain (1/10 on a VAS) during the late stance phase. In order to relieve this pain, the spacer was removed from beneath the anterior right protuberance. The protuberance was fixed back to its position. This brought the right ankle to a slightly plantar-flexed position. The patient then reported that he had no pain in the right ankle when walking with the device. The patient was then instructed to continue with the current total treatment time for a week so as to allow his neuromuscular control to get accustomed to the new calibration. Following that week, he was asked to increase the total treatment time by 15 minutes every week up to a maximum of 4 hours. He was also instructed, after the first week following the consultation, to go about indoor daily activities as normal when wearing the footwear.

On the third follow up the patient reported he did not have any pain in the right ankle. The gait lab parameters are presented in table 8. BP's with a convexity grade D were attached and fixed to the anterior and posterior BP's of both the right and the left devices. The hard spacer was removed from the right posterior protuberance. Following these changes, all BP's (on both right and left devices) were attached and fixed to their previous position. Clinical gait assessment with the device did not reveal any gait deviations and the patient reported he did not have any pain or discomfort. The patient was allowed to walk outside while wearing the footwear.

TABLE 8

Patient's Gait lab Parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1st (initial) | 65.1 | 43.8 | 50.2 | 43.2 | 31.7 |
| 2nd (first follow-up) | 78.0 | 48.9 | 52.3 | 41.09 | 33.2 |
| 3rd (second follow-up) | 105.5 | 54.3 | 57.1 | 39.5 | 37.8 |
| 4th (third follow-up) | 123.6 | 60.1 | 62.4 | 38.9 | 38.2 |

The invention claimed is:

1. A method of treating a subject afflicted with a lower limb joint pathology comprising the steps of:
   (a) securing a device to a subject's foot, whereby said device comprises a foot securing means, a support member operably attached to said securing means, and a ground engaging, moveable, anterior protuberance and a ground engaging, moveable, posterior protuberance protruding from an outsole, wherein said device supports the foot of said subject only by said anterior protuberance and said posterior protuberance when said anterior protuberance and said posterior protuberance are placed on a ground surface, wherein each of said posterior protuberance and said anterior protuberance comprises a base and a peak, wherein said moveable is moveable along an outer surface of said outsole within an area of 1 cm$^2$ to 18 cm$^2$; wherein said anterior protuberance and said posterior protuberance: (a) have a diameter of 50 to 150 mm; and (b) a shore hardness of 30 to 90 Sh A;
   (b) calibrating said posterior protuberance and said anterior protuberance to a balanced position, said balanced position comprises a position whereby said device provides a reduced inversion or a reduced eversion to said subject's foot during stance phases, said calibrating comprises manipulating: a step length, a single limb support, an out/in towing angle, a gait cycle, cadence, center of pressure, or any combination thereof, and
   (c) fixing said posterior protuberance and said anterior protuberance to said support member in said balanced position
   thereby treating a subject afflicted with a lower limb joint pathology.

2. The method of claim 1, whereby said calibrating further comprises adjusting: (a) a resilience of said anterior protuberance, said posterior protuberance, or a combination thereof; (b) a hardness of said anterior protuberance, said posterior protuberance, or a combination thereof; (c) an elasticity of said anterior protuberance, said posterior protuberance, or a combination thereof; (d) or any combination of (a), (b), and (c).

3. The method of claim 1, whereby said calibrating further comprises adjusting: (a) a height of said anterior protuberance, said posterior protuberance, or a combination thereof; (b) a convexity of said anterior protuberance, said posterior protuberance, or a combination thereof; (c) a weight of said anterior protuberance, said posterior protuberance, or a combination thereof; and (d) a combination of (a), (b), and (c).

4. The method of claim 1, whereby said balanced position further comprises balancing timing of heel rise.

5. The method of claim 1, whereby said balanced position further comprises toe balancing.

6. The method of claim 1, whereby said balanced position further comprises a position whereby reduced valgus, varus, dorsal or plantar torque about the ankle is exerted by said device on said subject's foot.

7. The method of claim 1, whereby said subject is further afflicted with pain and said balanced position is adapted to further comprise, a reduced lower limb musculoskeletal pain related to said pathology, position.

8. The method of claim 1, whereby said device is further adapted to treat lower limb osteoarthritis.

9. The method of claim 8, whereby said device is further adapted to treat knee osteoarthritis.

10. The method of claim 1, whereby said posterior protuberance is a bulbous protuberance, said anterior protuberance is a bulbous protuberance, or both said posterior protuberance and said anterior protuberance are bulbous protuberances.

11. The method of claim 1, whereby said anterior protuberance, said posterior protuberance, or their combination comprise a cross-section with a shape of a conic section, said conic section comprising at least one of a circle, ellipse, parabola and hyperbola.

12. The method of claim 1, whereby said anterior protuberance is shaped differently from the outer contour of said posterior protuberance.

13. A method of treating a subject afflicted with a lower limb musculoskeletal pain comprising the steps of:
   (a) securing a device to a subject's foot, whereby said device comprises a foot securing means, a support member operably attached to said securing means, and a ground engaging, moveable, anterior protuberance and a ground engaging, moveable, posterior protuberance protruding from an outsole, wherein said device supports the foot of said subject only by said anterior protuberance and said posterior protuberance when said anterior protuberance and said posterior protuberance are placed on a ground surface, wherein each of said posterior protuberance and said anterior protuberance comprises a base and a peak, wherein said moveable is moveable along an outer surface of said outsole within an area of 1 cm$^2$ to 18 cm$^2$; wherein said anterior protuberance and said posterior protuberance: (a) have a diameter of 50 to 150 mm; and (b) a shore hardness of 30 to 90 Sh A;
   (b) calibrating said posterior protuberance and said anterior protuberance to a balanced position, said balanced position comprises: a position whereby said device provides a reduced inversion or a reduced eversion to said subject's foot during the stance phases and a minimal lower limb musculoskeletal related pain position, said calibrating comprises manipulating: a step length, a single limb support, an out/in towing angle, a gait cycle, cadence, center of pressure, or any combination thereof; and (c) fixing said posterior protuberance and said anterior protuberance to said support member in said balanced position thereby treating a subject afflicted with a lower limb musculoskeletal pain.

14. The method of claim 13, whereby said calibrating further comprises adjusting: (a) a resilience of said anterior protuberance, said posterior protuberance, or a combination thereof; (b) a hardness of said anterior protuberance, said posterior protuberance, or said combination thereof; (c) an elasticity of said anterior protuberance, said posterior protuberance, or a combination thereof; (d) or any combination of (a), (b), and (c).

15. The method of claim 13, whereby said calibrating further comprises adjusting: (a) a height of said anterior protuberance, said posterior protuberance, or a combination thereof; (b) a convexity of said anterior protuberance, said posterior protuberance, or a combination thereof; and (c) a combination of (a) and (b).

16. The method of claim 13, whereby said balanced position further comprises balancing timing of heel rise.

17. The method of claim 13, whereby said balanced position further comprises toe balancing.

18. The method of claim 13, whereby said balanced position further comprises a position whereby reduced valgus, varus, dorsal or plantar torque about the ankle is exerted by said device on said subject's foot.

19. The method of claim 13, whereby said posterior protuberance is a bulbous protuberance, said anterior protuberance is a bulbous protuberance, or both said posterior protuberance and said anterior protuberance are bulbous protuberances.

20. The method of claim 13, whereby said anterior protuberance, said posterior protuberance, or their combination comprise a cross-section with a shape of a conic section, said conic section comprising at least one of a circle, ellipse, parabola and hyperbola.

21. The method of claim 13, whereby said anterior protuberance is shaped differently from the outer contour of said posterior protuberance.

22. The method of claim 13, whereby said device is further adapted to treat a lower limb joint pathology.

23. The method of claim 22, whereby said device is further adapted to treat lower limb osteoarthritis.

24. The method of claim 23, whereby said device is further adapted to treat knee osteoarthritis.

25. A device comprising a foot securing means, a support member operably attached to said securing means, and a ground engaging, moveable, anterior protuberance and a ground engaging, moveable, posterior protuberance protruding from an outsole, wherein said device supports the foot of a user only by said anterior protuberance and said posterior protuberance when said anterior protuberance and said posterior protuberance are placed on a ground surface, wherein each of said posterior protuberance and said anterior protuberance comprises a base and a peak, wherein said moveable is moveable along an outer surface of said outsole within an area of 1 $cm^2$ to 18 $cm^2$; wherein said anterior protuberance and said posterior protuberance: (a) have a diameter of 50 to 150 mm; and (b) a shore hardness of 30 to 90 Sh A; wherein said anterior protuberance and said posterior protuberance are positioned in a balanced position, said balanced position comprises a position: wherein said device is adapted to exert a reduced inversion or a reduced eversion during stance phases to said user's foot, said balanced position manipulates said user's: step length, single limb support, out/in towing angle, gait cycle, cadence, center of pressure, or any combination thereof.

26. The device of claim 25, wherein said posterior protuberance is a bulbous protuberance, said anterior protuberance is a bulbous protuberance, or both said posterior protuberance and said anterior protuberance are bulbous protuberances.

27. The device of claim 25, wherein said balanced position comprises a position wherein said device is adapted to exert a reduced valgus, varus, dorsal or plantar torque about the ankle of said user's foot.

* * * * *